(12) United States Patent
Miwa

(10) Patent No.: US 9,741,235 B2
(45) Date of Patent: Aug. 22, 2017

(54) DIGITAL REAL SECURITY SYSTEM, METHOD AND PROGRAM

(71) Applicant: TECHNOMIRAI Co., Ltd., Tokyo (JP)

(72) Inventor: Kazuo Miwa, Tokyo (JP)

(73) Assignee: TECHNOMIRAI CO., LTD., Tokyo (JP)

( * ) Notice: Subject to any disclaimer, the term of this patent is extended or adjusted under 35 U.S.C. 154(b) by 0 days.

(21) Appl. No.: 15/033,005

(22) PCT Filed: Feb. 21, 2014

(86) PCT No.: PCT/JP2014/054133
§ 371 (c)(1),
(2) Date: Apr. 28, 2016

(87) PCT Pub. No.: WO2015/064119
PCT Pub. Date: May 7, 2015

(65) Prior Publication Data
US 2016/0284201 A1 Sep. 29, 2016

(30) Foreign Application Priority Data

Oct. 28, 2013 (WO) .................. PCT/JP2013/079108

(51) Int. Cl.
*G08B 1/08* (2006.01)
*G08B 25/01* (2006.01)
(Continued)

(52) U.S. Cl.
CPC .............. *G08B 25/016* (2013.01); *A61B 5/08* (2013.01); *G01L 19/086* (2013.01);
(Continued)

(58) Field of Classification Search
None
See application file for complete search history.

(56) References Cited

U.S. PATENT DOCUMENTS

| 4,157,540 A | 6/1979 | Oros |
| 4,300,129 A | 11/1981 | Cataldo |
| 5,223,818 A | 6/1993 | Polo |

FOREIGN PATENT DOCUMENTS

| EP | 2871621 A1 | 5/2015 |
| JP | 2002-288771 A | 10/2002 |

(Continued)

OTHER PUBLICATIONS

International Search Report issued in Application No. PCT/JP2014/054133, Mailed May 27, 2014.

*Primary Examiner* — Adolf Dsouza
(74) *Attorney, Agent, or Firm* — Michael Best & Friedrich LLP

(57) ABSTRACT

A digital real security system, method and program reliably report the occurrence of an emergency situation in real time. The digital real security system comprises an abdominal pressure signal acquisition unit (101) that acquires an abdominal pressure signal from an abdominal pressure sensor (10) for detecting a user's abdominal pressure and acquires a respiration signal from a respiration sensor (20) for detecting the user's breathing, and a storage unit (105) that stores a normal-time number of breathing times and abdominal pressure pattern of the user detected by the abdominal pressure signal acquisition unit (101), and an abnormality determination unit (112) matches a number of breathing times and abdominal pressure pattern detected by the abdominal pressure signal acquisition unit (101) to that user's normal-time number of breathing times and abdominal pressure pattern stored in the storage unit (105), and determines whether it is abnormality based on the match result.

6 Claims, 15 Drawing Sheets

(51) Int. Cl.
  *G08B 25/08* (2006.01)
  *A61B 5/08* (2006.01)
  *G01L 19/08* (2006.01)
  *H04L 12/24* (2006.01)
  *H04W 4/22* (2009.01)
  *G08B 21/02* (2006.01)

(52) U.S. Cl.
  CPC ......... *G08B 21/0297* (2013.01); *G08B 25/08* (2013.01); *H04L 41/026* (2013.01); *H04W 4/22* (2013.01)

(56) References Cited

FOREIGN PATENT DOCUMENTS

| | | |
|---|---|---|
| JP | 2007-034848 A | 2/2007 |
| JP | 2011-050713 A | 3/2011 |
| JP | 5278981 B1 | 9/2013 |

F I G. 2

REGISTRATION SETTING INFORMATION

| USER 'A' | ABDOMINAL PRESSURE SENSOR A<br>NAME<br>MOBILE PHONE NUMBER<br>NORMAL-TIME ABDOMINAL PRESSURE INFORMATION | RESPIRATION SENSOR A<br>•NAME :<br>•MOBILE PHONE NUMBER :<br>•NORMAL-TIME RESPIRATORY INFORMATION | MOBILE TERMINAL A<br>•NAME :<br>•SENSOR NUMBER :<br>•DS2 INFORMATION :<br>•NORMAL-TIME INFORMATION<br>•ABDOMINAL PRESSURE PATTERN PROGRAM |
|---|---|---|---|
| USER 'B' | ABDOMINAL PRESSURE SENSOR B<br>NAME<br>MOBILE PHONE NUMBER<br>NORMAL-TIME ABDOMINAL PRESSURE INFORMATION | RESPIRATION SENSOR B<br>•NAME :<br>•MOBILE PHONE NUMBER :<br>•NORMAL-TIME RESPIRATORY INFORMATION | MOBILE TERMINAL B<br>•NAME :<br>•SENSOR NUMBER :<br>•DS2 INFORMATION :<br>•NORMAL-TIME INFORMATION<br>•ABDOMINAL PRESSURE PATTERN PROGRAM |
| USER 'C' | ABDOMINAL PRESSURE SENSOR C<br>NAME<br>MOBILE PHONE NUMBER<br>NORMAL-TIME ABDOMINAL PRESSURE INFORMATION | RESPIRATION SENSOR C<br>•NAME :<br>•MOBILE PHONE NUMBER :<br>•NORMAL-TIME RESPIRATORY INFORMATION | MOBILE TERMINAL C<br>•NAME :<br>•SENSOR NUMBERS :<br>•DS2 INFORMATION :<br>•NORMAL-TIME INFORMATION<br>•ABDOMINAL PRESSURE PATTERN PROGRAM |

120

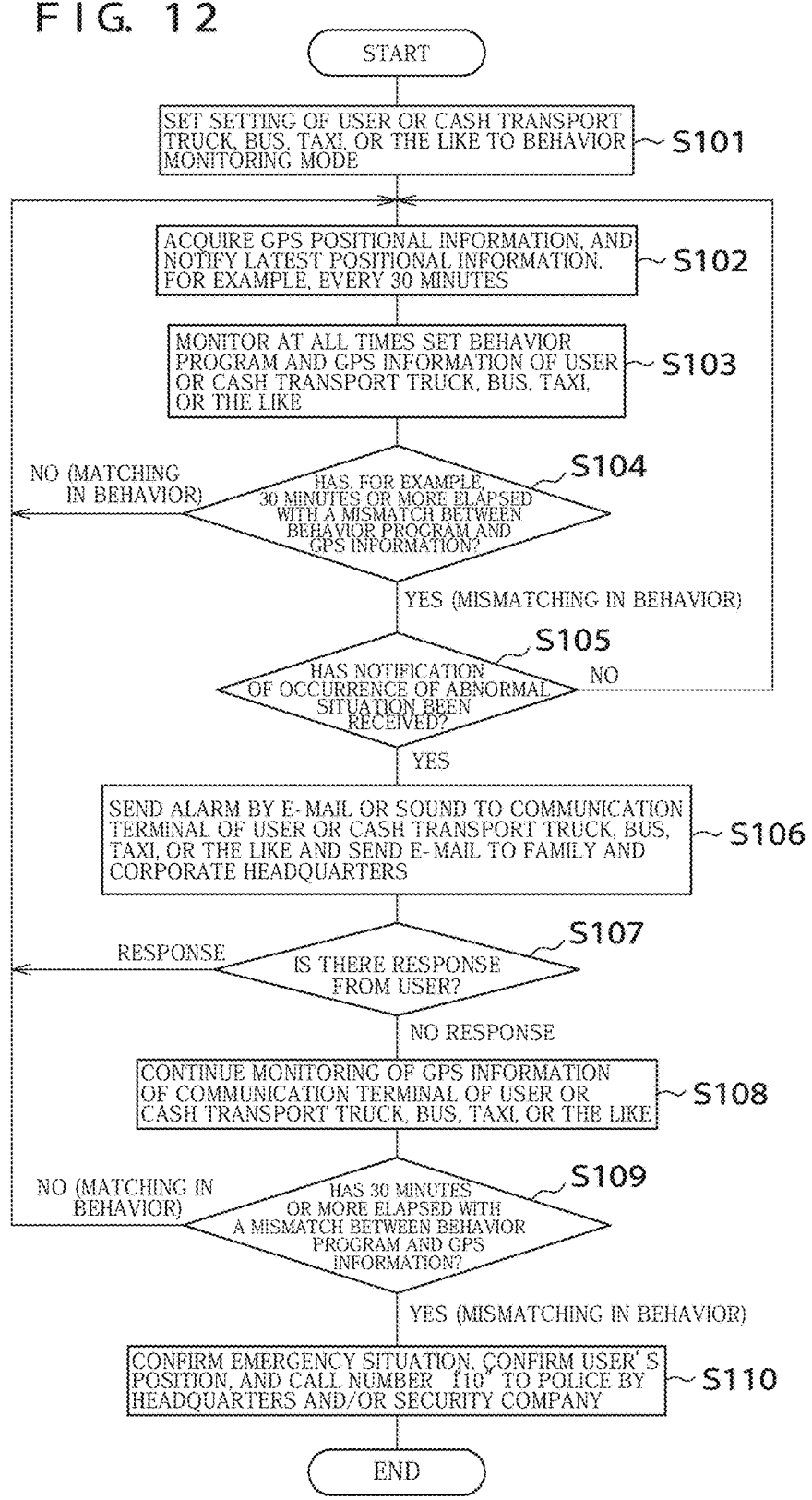

F I G. 13

| USER | NORMAL ABDOMINAL PRESSURE | ABNORMAL STATE | INTENTIONAL ABDOMINAL PRESSURE SET BY INDIVIDUAL | ABDOMINAL PRESSURE PATTERN | EMERGENCY SITUATION |
|---|---|---|---|---|---|
| USER A | NORMAL ABDOMINAL PRESSURE | i. ATTENTION<br>ii. ABNORMAL SITUATION<br>iii. EMERGENCY STATE | I PATTERN<br>II PATTERN<br>III PATTERN | REPEAT I TO III PATTERNS 1 TO 2 TIMES TO INCREASE SENSITIVITY AND ACCURATELY TRANSMIT THE ABNORMAL SITUATION IN REAL TIME TO THE CORPORATE HEADQUARTERS, SECURITY COMPANY, AND FAMILY | USER A'S ABDOMINAL PRESSURE SIGNALS ARE TRANSMITTED TO USER A'S MOBILE TERMINAL, AND THE MOBILE TERMINAL CHECKS WITH USER A'S ABDOMINAL PRESSURE PROGRAM, AND SENDS AN EMERGENCY TRANSMISSION TO THE CORPORATE HEADQUARTERS AND FAMILY NOTIFYING THAT USER A IS IN AN EMERGENCY |
| ... | | | | | |
| USER Z | | | | | |

FIG. 16 (A)

*CHEST/ABDOMINAL MOTION NUMERICAL SETTING EXAMPLE
IN NORMAL RESPIRATION TIME

| INITIAL SETTING : | n | | |
|---|---|---|---|
| CHEST A: BREATHE IN | 1,057mm | CHEST B: BREATHE OUT | 1,010mm |
| ABDOMEN A: BREATHE IN | 930mm | ABDOMEN B: BREATHE OUT | 925mm |
| | | | |

NUMBER OF BREATHING TIMES

*CHEST/ABDOMINAL MOTION NUMERICAL SETTING EXAMPLE
IN NORMAL RESPIRATION TIME

| INITIAL SETTING : | n+1 | | |
|---|---|---|---|
| CHEST A: BREATHE IN | 1,060mm | CHEST B: BREATHE OUT | 1,013mm |
| ABDOMEN A: BREATHE IN | 933mm | ABDOMEN B: BREATHE OUT | 928mm |
| | | | |

NUMBER OF BREATHING TIMES

26

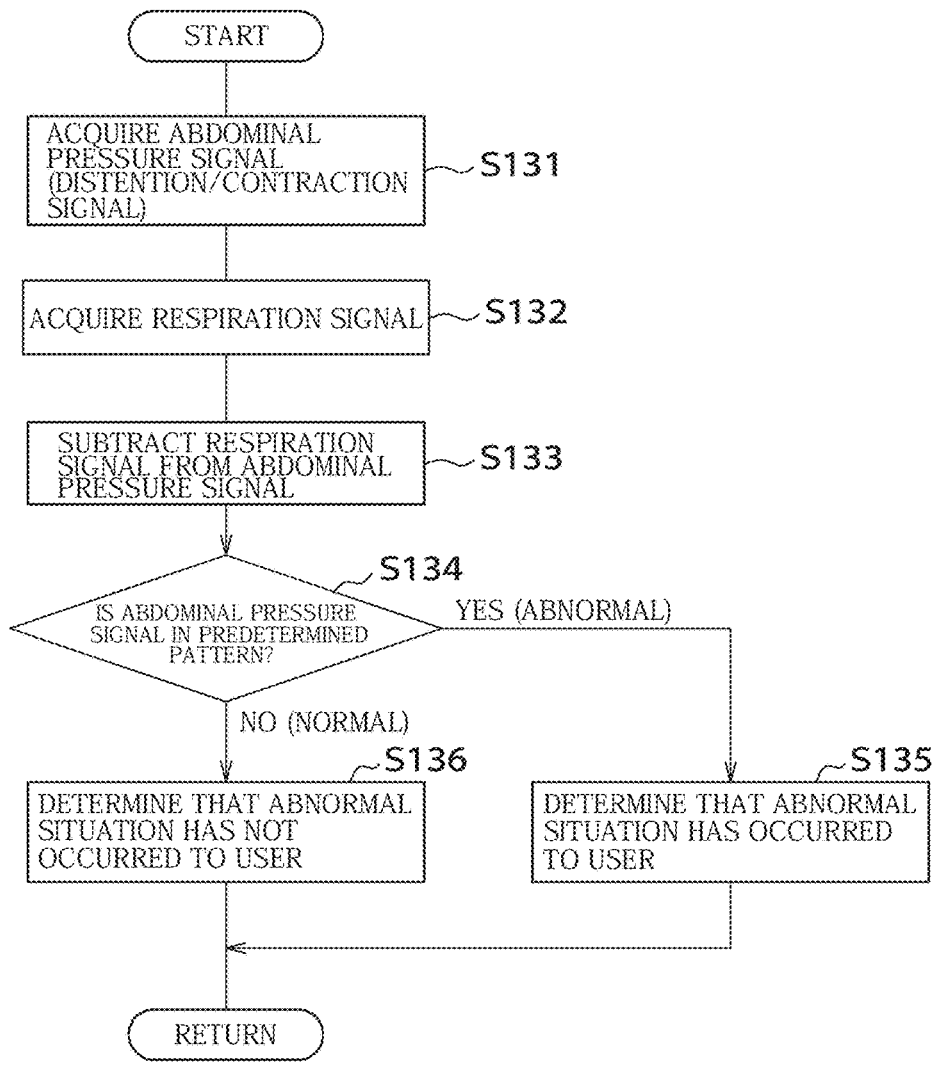

DIGITAL REAL SECURITY SYSTEM, METHOD AND PROGRAM

TECHNICAL FIELD

The present invention relates to a digital real security system, method and a program that allow reporting an abnormal situation in security, even in front of a suspicious person, without the suspicious person's awareness.

BACKGROUND ART

Service operations such as stores including department stores, supermarkets, and convenience stores, banks, company offices, factories, event halls, air terminals, money exchangers, cash transport trucks, buses, and taxies have been handling financial paper, cash, and/or commodities. Their customers include not only well-intentioned persons but also those having criminal intent, so that there is a high risk of crime victimization along with operating activities.

In an emergency, it is common that the victim notifies the emergency situation to his/her family, corporate concerned person, the police, and/or the like and waits for help. However, the victim threatened by the perpetrator is restricted from any actions, which leads to trouble or an incident in many cases.

Conventionally, as a device that performs transmission of an emergency signal in a situation of being incapable of freely moving, a device has been provided which is fitted to a user's belt and performs the transmission based on sensing a change in tension on the belt when the user tenses his/her abdomen.

Patent Literature 1 describes an emergency transmitter which transmits an emergency signal by a user applying his/her abdominal pressure and includes a pressure detection unit for detecting pressure applied to a contact surface, a transmission unit for transmitting an emergency signal, and a control unit for, when it is determined to be abnormal based on an output of the pressure detection unit, causing the transmission unit to transmit an emergency signal therefrom. The emergency transmitter described in Patent Literature 1 transmits an emergency signal based on, for example, a convenience store clerk or a bank clerk tensing his/her abdomen even in a situation of being incapable of freely moving.

The emergency transmitter described in Patent Literature 1, in order to prevent erroneous reports and failed reports caused by adjustment of the tightness of the belt and the like, adopts a configuration of further including a cancel switch, for determining it to be abnormal unless a cancellation signal is input within a predetermined time.

But, even if such a cancellation switch is provided, all erroneous reports and failed reports cannot be prevented. That is, because the emergency transmitter described in Patent Literature 1 remains a configuration of sensing a user's abdominal pressure to determine abnormality, when a signal to sense an abdominal pressure itself contains noise associated with breathing, the magnitude and timing of the abdominal pressure may be erroneously detected due to the noise.

CITATION LIST

Patent Literature

[Patent Literature 1] JP 2002-288771 A

SUMMARY OF INVENTION

Technical Problem

Further, the emergency transmitter described in Patent Literature 1 does not assume to the point in which a thug robs a user of said device. In this case, if the thug leaves said device as it is, there is a possibility that the occurrence of abnormality can be sensed by a judgment of the situation such as the absence of a response to a regular transmission or a call. However, there has been a problem of the lack of real-timeness to a time-sensitive situation. Also, when the thug knows the mechanism of said device and wears it on him/herself or a third person without leaving, it is difficult to detect the occurrence of abnormality.

It is an object of the present invention to provide a digital real security system, method and a program that allow reliably reporting the occurrence of an emergency situation in real time.

Solution to Problem

A digital real security system according to the present invention comprises abdominal pressure signal acquiring means for acquiring an abdominal pressure signal from an abdominal pressure sensor for detecting an abdominal pressure of personnel to which the abdominal pressure sensor is fitted; abdominal pressure signal extracting means for extracting from the acquired abdominal pressure signal an abdominal pressure pattern in which abdominal pressure changes and/or a number of breathing times per unit time; storage means for storing a normal-time abdominal pressure pattern and/or number of breathing times of the personnel extracted by the abdominal pressure signal extracting means in association with the personnel; abnormality determining means for matching the abdominal pressure pattern and/or number of breathing times extracted by the abdominal pressure signal extracting means to the personnel's normal-time abdominal pressure pattern and/or number of breathing times stored in the storage means, and determining whether it is abnormality based on the match result; and control means for reporting an abnormal situation according to the abnormality determination result by the abnormality determining means.

Also, the abdominal pressure signal extracting means subtracts the respiration signal component from the acquired abdominal pressure signal, and extracts an abdominal pressure pattern from an abdominal pressure signal with suppressed influence of respiration, which allows accurately determining a personnel's intentional abnormality.

Also, the abnormality determining means determines that it is abnormality if the match result of the abdominal pressure pattern and/or number of breathing times extracted by the abdominal pressure signal extracting means with the personnel's normal-time abdominal pressure pattern and/or number of breathing times stored in the storage means is a mismatch, which enables matching verification even when a thug robs the user of a chest/abdominal motion signal detection device 300 and wears the same, to allow determining an abnormal situation so as to allow reporting the abnormal situation.

Also, the control means makes a different report according to the abnormality determination result of the abnormality determining means, which allows making a detailed report according to the details or degree of an abnormal situation.

Also, the reporting means transmits an e-mail message and an image, which allows a person having received a report to assess the abnormal situation accurately and promptly.

A digital real security method according to the present invention comprises an abdominal pressure signal acquiring step of acquiring an abdominal pressure signal from an abdominal pressure sensor for detecting an abdominal pressure of personnel to which the abdominal pressure sensor is fitted; an abdominal pressure signal extracting step of extracting from the acquired abdominal pressure signal an abdominal pressure pattern in which abdominal pressure changes and/or a number of breathing times per unit time; a storing step of storing a normal-time abdominal pressure pattern and/or number of breathing times of the personnel extracted by the abdominal pressure signal extracting step in association with the personnel; an abnormality determining step of matching the abdominal pressure pattern and/or number of breathing times extracted by the abdominal pressure signal extracting step to the personnel's normal-time abdominal pressure pattern and/or number of breathing times stored by the storing step, and determining whether it is abnormality based on the match result; and a control step of reporting an abnormal situation according to the abnormality determination result by the abnormality determining step.

The present invention is also a program for causing a computer to function as a digital real security system including abdominal pressure signal acquiring means for acquiring an abdominal pressure signal from an abdominal pressure sensor for detecting an abdominal pressure of personnel to which the abdominal pressure sensor is fitted, abdominal pressure signal extracting means for extracting from the acquired abdominal pressure signal an abdominal pressure pattern in which abdominal pressure changes and/or a number of breathing times per unit time, storage means for storing a normal-time abdominal pressure pattern and/or number of breathing times of the personnel extracted by the abdominal pressure signal extracting means in association with the personnel, abnormality determining means for matching the abdominal pressure pattern and/or number of breathing times extracted by the abdominal pressure signal extracting means to the personnel's normal-time abdominal pressure pattern and/or number of breathing times stored in the storage means, and determining whether it is abnormality based on the match result, and control means for reporting an abnormal situation according to the abnormality determination result by the abnormality determining means.

Advantageous Effects of Invention

The present invention allows reliably reporting the occurrence of an emergency situation in real time. The present invention allows reporting an abnormal situation even when a thug robs a user of the present sensor and wears the same.

BRIEF DESCRIPTION OF DRAWINGS

FIG. 2 is a chart showing registration setting information of abdominal pressure sensors, respiration sensors, and communication terminals of the digital real security system according to the first embodiment of the present invention.

FIG. 12 is a flowchart showing a behavior monitoring control operation of a monitoring device of a digital real security system according to a second embodiment of the present invention.

FIG. 13 is a chart showing an example of abdominal pressure patterns of a digital real security system according to a third embodiment of the present invention.

FIG. 16(A) and FIG. 16(B) are charts each showing an example of chest/abdominal motion numerical settings in user's normal respiration time of the digital real security system according to the fourth embodiment of the present invention.

FIG. 17 is a flowchart showing an abdominal pressure abnormality determining processing by an abnormality determination unit of the communication terminal of the digital real security system according to the fourth embodiment of the present invention.

DESCRIPTION OF EMBODIMENTS

Hereinafter, modes for carrying out the present invention will be described in detail with reference to the accompanying drawings.

(First Embodiment)

Figure 1:
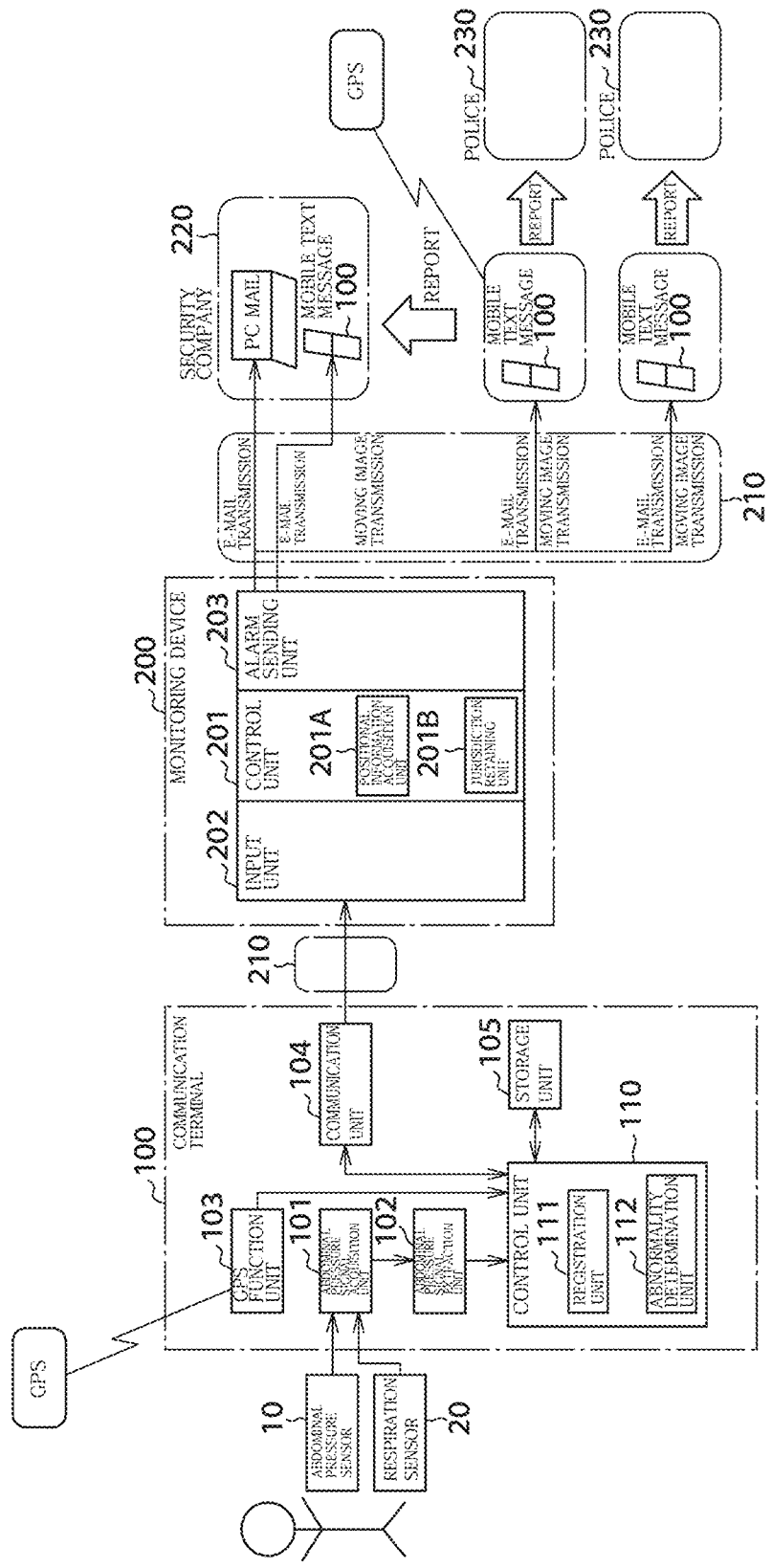
FIG. 1 is a block diagram showing a configuration of a digital real security system according to a first embodiment of the present invention.

FIG. 1 is a block diagram showing a configuration of a digital real security system according to a first embodiment of the present invention.

The present digital real security system comprises a communication terminal 100 capable of receiving respiratory information from an abdominal pressure sensor 10 that is worn on a user (personnel) and for sensing abdominal distention and contraction to output an abdominal pressure signal and a respiration sensor 20 for detecting human respiration to output a respiration signal, and a monitoring device 200 being a main body of digital real security system equipment that communicates with the communication terminal 100 via a telephone line 210.

In addition, when the digital real security system provides services of a security contract to the communication terminals 100, users of the communication terminals 100 can be referred to as users from the viewpoint of the digital real security system.

Also, depending on the intended use, the configuration may be such that the monitoring device 200 is incorporated into the communication terminal 100, but in the present embodiment, description will be given of a configuration for which the communication terminal 100 and the monitoring device 200 are separated.

The communication terminals 100 consist of mobile phones, PHS (Personal Handy-Phone System) phones, PDAs (Personal Digital Assistants), smartphones, or the like, and transmit a sound transmission and a repelling device operating command to the monitoring device 200 via the telephone line 210. In the present embodiment, mobile phones or smartphones are used as the communication terminals 100, and each individual can use the same at a variety of locations (that is, current position). One of the communication terminals 100 is disposed at a security company 220 together with a PC (Personal Computer). The communication terminal 100 is capable of receiving an e-mail message, an image including a moving image, or the like from the monitoring device 200 via the telephone line 210.

[Abdominal Pressure Sensor 10]

The abdominal pressure sensor 10 senses user's abdominal distention and contraction to output a distention/contraction signal (abdominal pressure signal). An abdominal pressure can be detected based on the distention/contraction signal. Here, the distention/contraction signal is considered to be superimposed with a respiration signal component being a component of a respiratory. The abdominal pressure sensor 10 is fitted to, for example, the user's belt or the like to detect a pressure from the user's abdomen. For the pressure sensor to detect pressure, a pressure sensitive sensor can be used. The pressure sensitive sensor detects a pressure applied to a sensing surface and continuously outputs a voltage value according to the detected value. The output value of the pressure sensitive sensor is determined by the magnitude of applied pressure and the magnitude of the area having received the pressure. The abdominal pressure signal acquired by the abdominal pressure sensor 10 is output to the communication terminal 100 which is the subject of the present invention according to a wireless communication system.

In addition, the details of abdominal pressure detection that senses abdominal distention and contraction to detect abdominal pressure by the abdominal pressure sensor 10 will be described later according to FIG. 2.

[Respiration Sensor 20]

The respiration sensor 20 captures movements of the body surface due to respiration. Although not being the subject of the present invention, the respiration sensor 20 will be described for the sake of understanding the present invention. The respiration sensor 20 senses respiration (whether the respiratory rate is high or low, breathing or not) based on minute body movements, for example, using a microwave Doppler sensor, by microwaves (2.4 GHz) sent from the sensor. The respiration sensor 20, using an adhesive sensor having a built-in acoustic transducer as another example, distinguishes between air flows (inhalation and expiration) in the respiratory tract to detect the respiratory rate successively. The respiration signal acquired by the respiration sensor 20 is output to the communication terminal 100 which is the subject of the present invention according to a wireless communication system.

Here, the abdominal pressure sensor 10 is at all times sending an abdominal distention/contraction signal to the communication terminal 100. Moreover, the respiration sensor 20 is also at all times sending a respiration signal to the communication terminal 100.

In addition, in the present embodiment, the abdominal pressure sensor 10 is fitted to a user's abdomen (for example, a belt) and the respiration sensor 20 is fitted to the user's body surface. However, the abdominal pressure sensor 10 and the respiration sensor 20 may be an integral configuration. The abdominal pressure respiration signal by the abdominal pressure sensor 10 and the respiration signal by the respiration sensor 20 are transmitted to the communication terminal 100. The abdominal pressure sensor 10 and the respiration sensor 20 are worn on an employee(s) and the like who wishes to transmit an emergency signal at intrusion of a robber(s), such as for example an employee(s) of a store including a convenience store or a bank. Also, as in a second embodiment to be described later, the abdominal pressure sensor 10 and the respiration sensor 20 may be worn on an employee(s) of a cash transport truck, bus, taxi, or the like.

[Communication Terminal 100]

The communication terminal 100 is configured including an abdominal pressure signal acquisition unit 101 that acquires an abdominal pressure signal from the abdominal pressure sensor 10 and a respiration signal from the respiration sensor 20, an abdominal pressure signal extraction unit 102 that subtracts the respiration signal component from the acquired abdominal pressure signal to extract an abdominal pressure signal with suppressed influence of respiration, a GPS (Global Positioning System) function unit 103, a communication unit 104, a storage unit 105, and a control unit 110 that controls the communication terminal as a whole.

The abdominal pressure signal acquisition unit 101 acquires an abdominal pressure signal detected by the abdominal pressure sensor 10 and a respiration signal detected by the respiration sensor 20 wirelessly or by a wire. Examples of the wireless communication system are Bluetooth (registered trademark), Wi-Fi (Wireless Fidelity) radio including IEEE802.11b standards, specified low power radio, ultra-wideband transmission systems such as UWB (Ultra Wide Band), and infrared communication. Also, a wire connection by an interface such as a USB (Universal Serial Bus) is also available.

The abdominal pressure signal extraction unit 102 subtracts, as noise, from an acquired distention/contraction signal, a respiration signal component of the respiration sensor 20 superimposed on the distention/contraction signal using a signal processing circuit such as for example a DSP (Digital Signal Processor) to extract a distention/contraction signal with suppressed influence of respiration.

The GPS function unit 103 receives radio waves of positional information from a GPS satellite or the like. The GPS function unit 103 calculates, from information received via a GPS antenna, current positional information as two parameters of the latitude and longitude to acquire positional information. In general, altitude information can also be acquired by the GPS, but is not used in the present embodiment.

In addition, in the present embodiment, the example using a GPS satellite has been mentioned as a means for acquiring positional information, but it may be a system other than the GPS using a positional relationship with a base station. For example, when an Android (registered trademark) smartphone or a highly functional mobile phone with a camera is used as the communication terminal 100 being a mobile terminal, it is also possible to acquire current positional information of its own terminal through approach checking by performing transmission/reception of information with a mobile phone company server via a base station and mobile telephone communication network (not shown) used in place of the GPS function unit 103 or in combination therewith.

Also, positional information acquisition by Wi-Fi positioning, that is, positional information acquisition using a Wi-Fi access point and a predetermined positional information service may be used.

Similar to an ordinary communication terminal, the communication unit 104 performs transmission/reception with a base station. In the present embodiment, the communication terminal 100, to the monitoring device 200 via the communication unit 104, transmits positional information of the communication terminal 100 every certain period of time, and transmits notification of the occurrence of abnormality and the latest positional information on the occurrence of an abnormal situation.

The storage unit 105 is formed by a nonvolatile memory such as an EEPROM (Electrically Erasable Programmable Read-Only Memory), and holds information even after the main body is powered off. The storage unit 105 stores ID information of its own terminal, registration setting information (refer to FIG. 2) to acquire abdominal pressure information from the abdominal pressure sensor 10, registration setting information (refer to FIG. 2) to acquire respiratory information from the respiration sensor 20, and an abdominal pressure pattern program to determine the occurrence of abnormality.

The control unit 110 is formed by a CPU (Central Processing Unit) or the like, and performs control of the communication terminal 100 as a whole, and performs control to determine the occurrence of an abnormal situation and reports the abnormal situation.

The control unit 110 includes a registration unit 111 that registers registration setting information to acquire respiratory information, and an abnormality determination unit 112 that determines the occurrence of an abnormal situation based on an abdominal pressure signal from which the respiration signal component has been subtracted.

To the abnormality determination unit 112, an abdominal pressure signal extracted by the abdominal pressure signal extraction unit 102 is repeatedly transmitted. When the abdominal pressure signal indicates an abnormal situation, it is determined that an abnormal situation has occurred. In general, the abdomen distends and contracts in accordance with breathing in normal time, but sometimes distends and contracts independently of breathing. Thus, simply determining a mere change in extracted abdominal pressure signal to be an abnormality results in an erroneous report. Therefore, a person's intentional distention/contraction is detected to determine an abnormality. The determination can be in the case such as where the abdominal pressure signal has an unusual magnitude, where the speed of a change in the abdominal pressure signal has an unusual magnitude, or where a change in the abdominal pressure signal has an unusual pattern (abdominal pressure pattern).

The registration unit 111 and the abnormality determination unit 112 are programs. In the following, when the subject is described as "the XX unit," the CPU reads out an abdominal pressure pattern program from the storage unit 105 as needed and then loads the same in a main storage unit (not shown), and executes respective functions (described later). The abdominal pressure pattern program may be stored in advance in the storage unit 105, or may be taken into the communication terminal 100 when necessary via another storage medium or communication medium.

[Monitoring Device 200]

The monitoring device 200 comprises a control unit 201, an input unit 202, and an alarm sending unit 203. The monitoring device 200 may be a common server computer, a personal computer, or the like.

The control unit 201 is formed by a CPU or the like, and controls the device as a whole and executes a security program to function as a digital real security system. The control unit 201 has a memory (not shown) to store information. A semiconductor memory such as an SD (Secure Digital) card, a USB (Universal Serial Bus) memory, or a memory stick (Memory Stick), a magnetic recording device, an optical disk device, a magneto-optical disk drive device, or the like can be the memory.

The control unit 201 comprises a positional information acquisition unit 201a that tracks an existing position of the communication terminal 100 serving as an information addressee, and acquires positional information of the communication terminal 100, and a jurisdiction retaining unit 201b that retains a police jurisdictional district where a mobile phone exists. Here, the police jurisdictional districts to receive mobile phone calls are on a prefecture-by-prefecture basis in Japan. The control unit 201, when having detected an emergency situation, performs control to specify a communication terminal 100 serving as an information addressee that exists in the police jurisdictional district where the communication terminal 100 serving as an information addresser with reference to the jurisdiction retaining unit 201b, and to report preferentially to the specified communication terminal 100.

The control unit 201 judges a sound transmission (warning to an intruder) and a repelling device operating command transmitted from the communication terminal 100 having received a report, and if these commands are as such, can even output a sound signal to a speaker (not shown) via the input unit 202, and output an operation signal to a repelling device (not shown).

The input unit 202 has a function as an abnormal situation detecting means that detects an abnormal situation based on an abnormality determination result from the communication terminal 100 serving as an information addresser. The input unit 202 receives positional information of the respective communication terminals 100 transmitted from the communication terminal 100 via the telephone line 210, and outputs these signals to the control unit 201.

The alarm sending unit 203 transmits an e-mail message or an image including a moving image to other communication terminals 100 and the security company 220 via the telephone line 210.

The security company 220, when having received an e-mail message, an image, or the like from the present digital real security system, performs investigation on the abnormal situation. In addition, the security company 220 is not an essential structural element of the digital real security system according to the present embodiment.

[Registration Setting Information]

FIG. 2 is a chart showing registration setting information of the abdominal pressure sensors 10, the respiration sensors 20, and the communication terminals 100.

As shown in FIG. 2, the storage unit 105 of the communication terminal 100 has stored registration setting information 120 that is referred to when an abdominal pressure pattern program is executed. Respiratory information of the communication terminal 100 are set as the registration setting information 120 associated with the abdominal pressure sensor 10 and the respiration sensor 20 for each user of the present system. This registration setting information 120 is in advance transferred to the monitoring device 200 and registered in the monitoring device 200, and also in the monitoring device 200, abdominal pressure information of the communication terminal 100 of each user of the present system can be referred to.

As the registration setting information 120, the abdominal pressure sensor 10 and the respiration sensor 20 and the communication terminal 100 are associated with each other for each user. Specifically, the user's name, mobile phone number, and normal-time abdominal pressure information are items on the side of the abdominal pressure sensor 10, the user's name, mobile phone number, and normal-time respiratory information are items on the side of the respiration sensor 20, and the user's name, abdominal pressure sensor number, respiration sensor number, monitoring device 200 (DS2) information, normal-time abdominal pressure information, and normal-time respiratory information are for the communication terminal 100. Also, in the storage unit 105, an abdominal pressure pattern program is registered. The abdominal pressure pattern program is registered in the communication terminal 100 and the monitoring device 200 respectively.

Hereinafter, the operation of the digital real security system configured as described above will be described.

[Registration Processing]

First, a registration processing of the abdominal pressure sensor 10, the respiration sensor 20, the communication terminal 100, and the monitoring device 200 will be described.

Figure 3:
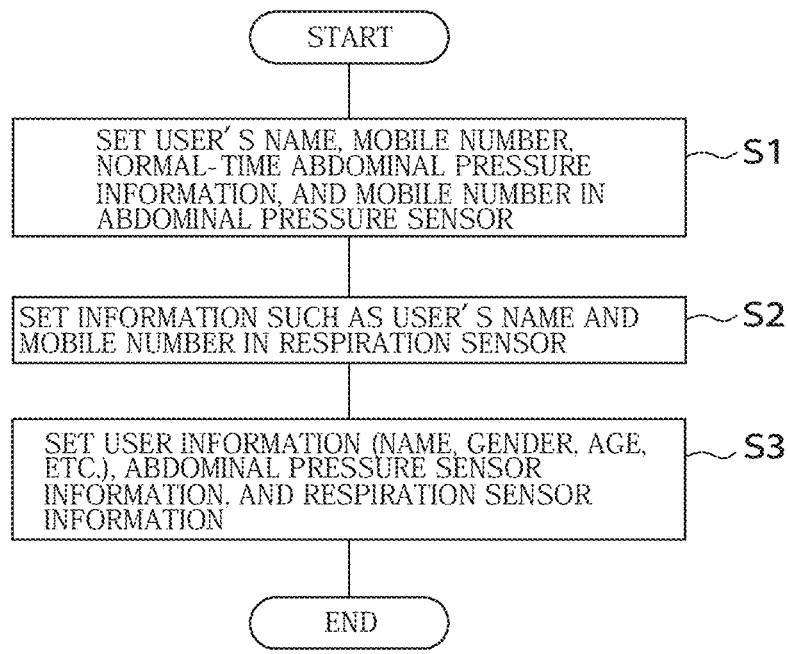
FIG. 3 is a flowchart showing a registration processing of the respiration sensor and communication terminal of the digital real security system according to the first embodiment of the present invention.

FIG. 3 is a flowchart showing a registration processing of the abdominal pressure sensor 10, the respiration sensor 20, and the communication terminal 100. The present flow is executed mainly by the registration unit 111 (FIG. 1) of the control unit 110 of the communication terminal 100.

In step S1, the user sets the user's name, mobile phone number, and normal-time abdominal pressure information and the mobile phone number of the communication terminal 100 to which detected abdominal pressure information is transmitted in the abdominal pressure sensor 10.

In step S2, the user sets the user's name, mobile phone number, and normal-time abdominal pressure information and the mobile phone number of the communication terminal 100 to which detected respiratory information is transmitted in the respiration sensor 20.

In step S3, the registration unit 111 sets user information (name, gender, age, etc.), abdominal pressure sensor information, and respiration sensor information by a pairing operation using a wireless communication system such as Bluetooth or specified low power radio with the abdominal pressure sensor 10 and the respiration sensor 20, and registers the information in the storage unit 105 as registration setting information 120 (refer to FIG. 2). It is preferable to have stored the type of business of users to which the present system is mainly applied as the above-described user information, besides basic information such as the name, gender, and age, in order to enhance effectiveness in the case of security by the digital real security system.

Next, a registration processing of the abdominal pressure sensor 10, the respiration sensor 20, the communication terminal 100, and the monitoring device 200 will be described.

Figure 4:
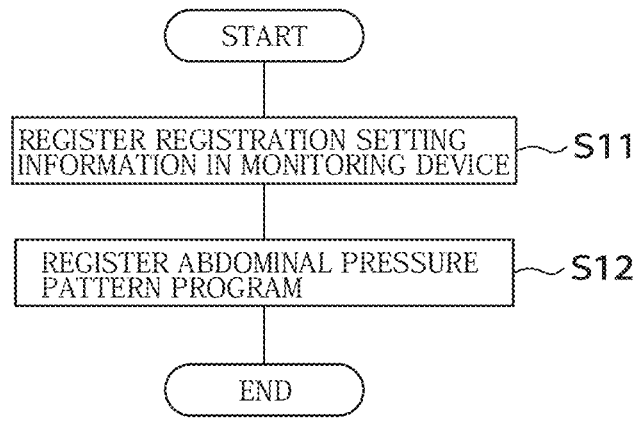
FIG. 4 is a flowchart showing a registration processing of a monitoring device of the digital real security system according to the first embodiment of the present invention.

FIG. 4 is a flowchart showing a registration processing of the monitoring device 200 (FIG. 1). The present flow is executed mainly by the control unit 201 of the monitoring device 200.

In step S11, the control unit 201 registers user information transmitted from the communication terminal 100, in advance, as monitoring device registration setting information (not shown). As the monitoring device registration setting information, user information of the abdominal pressure sensor 10 and the respiration sensor 20 correlated with the communication terminal 100, the mobile phone number of the communication terminal, the name, a password, a contact address, normal-time respiratory information, etc., are registered.

In step S12, the control unit 201 registers an abdominal pressure pattern program representing an abdominal pressure pattern.

[Terminal Monitoring Control]

Next, monitoring control of the communication terminal 100 of the digital real security system will be described.

Figure 5:
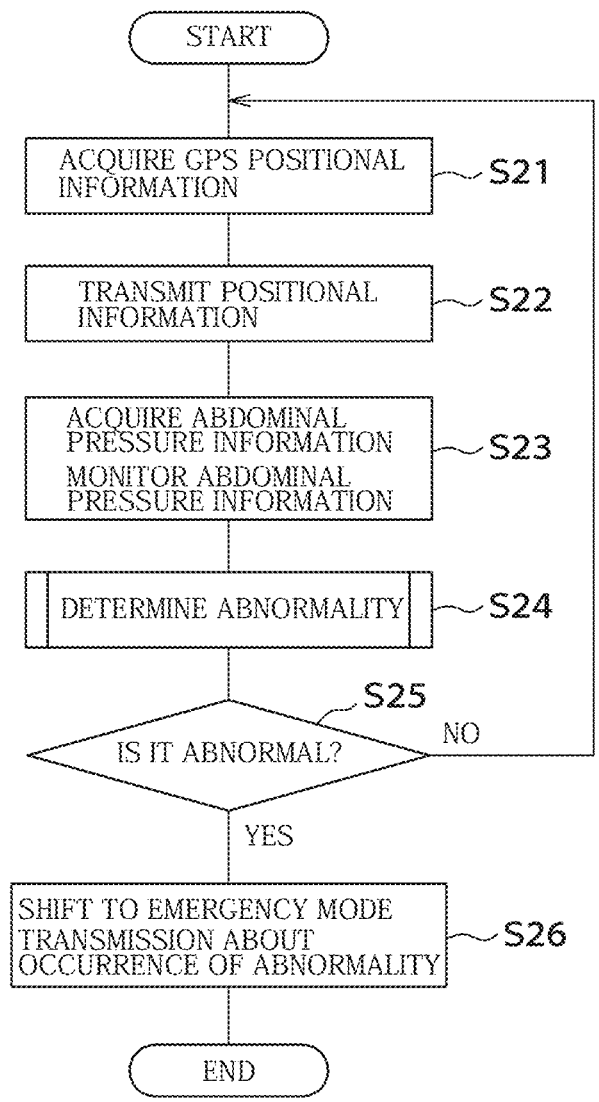
FIG. 5 is a flowchart showing a monitoring control processing of a communication terminal of the digital real security system according to the first embodiment of the present invention.

FIG. 5 is a flowchart showing a monitoring control processing of the communication terminal 100 of the digital real security system. The present flow is executed mainly by the control unit 110 (FIG. 1) of the communication terminal 100.

First, in step S21, the GPS function unit 103 acquires current positional information of the communication terminal 100.

In step S22, the control unit 110 transmits acquired positional information of the communication terminal 100 via the communication unit 104 to the monitoring device 200 every predetermined time (for example, one hour). The control unit 201 of the monitoring device 200 receives the positional information from the communication terminal 100 by the input unit 202. The monitoring device 200 can thereby be informed of the latest positional information of the communication terminal 100, for example, every one hour. In the present embodiment, it is assumed that the user carries the abdominal pressure sensor 10, the respiration sensor 20, and the communication terminal 100 with him/her. Therefore, the monitoring device 200 can be informed of the current position of the user that uses the abdominal pressure sensor 10 and the respiration sensor 20.

In addition, if system resources allow, a position closer to the current position can be informed by setting the above-described predetermined time to, for example, every 10 minutes. Alternatively, there may be a mode of changing the above-described predetermined time according to the degree of emergency, necessity, or importance. Here, the positional information of the user (communication terminal 100) is an example of a more preferred embodiment of a digital real security system, and is not essential. That is, it suffices that an abnormal change in the user based on a user's abdominal pressure pattern can be determined using the abdominal pressure sensor 10 and the respiration sensor 20 on the side of the monitoring device 200. There is a unique effect that an abnormal change in the user can be informed without the attacker's awareness or the like. However, if not only informing an abnormal change in a user but the current position of said user (communication terminal 100) can also be informed, a more appropriate response can be taken.

In step S23, the abdominal pressure signal acquisition unit 101 acquires at all times an abdominal pressure signal and a respiration signal of the user's abdominal pressure sensor 10 and the respiration sensor 20, respectively, and the control unit 110 monitors the acquired user's abdominal pressure signal and respiration signal.

In step S24, the control unit 110 starts the abdominal pressure pattern program, and determines abnormality in user's abdominal pressure based on the abdominal pressure information and respiratory information. The details of an abdominal pressure abnormality determination will be described later according to FIG. 6.

In step S25, the abnormality determination unit 112 determines whether the user's abdominal pressure is abnormal, and if the user's abdominal pressure is abnormal, the processing shifts to step S26, and if the user's abdominal pressure is not abnormal, the processing returns to the above-described step S21.

In step S26, the control unit 110 shifts to an emergency mode to transmit an e-mail message about the occurrence of abnormality to the monitoring device 200 via the communication unit 104 and transmit the latest positional information of the communication terminal 100. In addition, if it takes a long time to acquire the latest positional information of the communication terminal 100 (such as a failure in acquiring GPS positional information) in the emergency mode, it is preferable to be a mode of first causing notification of the occurrence of abnormality without waiting for the acquisition of the latest positional information. Also, the positional information acquired last time may be transmitted. This allows reliably reporting an abnormal situation by the user's intention without the robber's awareness.

In the present embodiment, the abdominal pressure sensor 10 is at all times sending an abdominal distention/contraction signal to the communication terminal 100, and moreover, the respiration sensor 20 is also at all times sending a respiration signal to the communication terminal 100, and therefore, the communication terminal 100 can determine an abnormal state in real time based on an extracted abdominal pressure signal.

[Abnormality Determining Processing]

Figure 6:
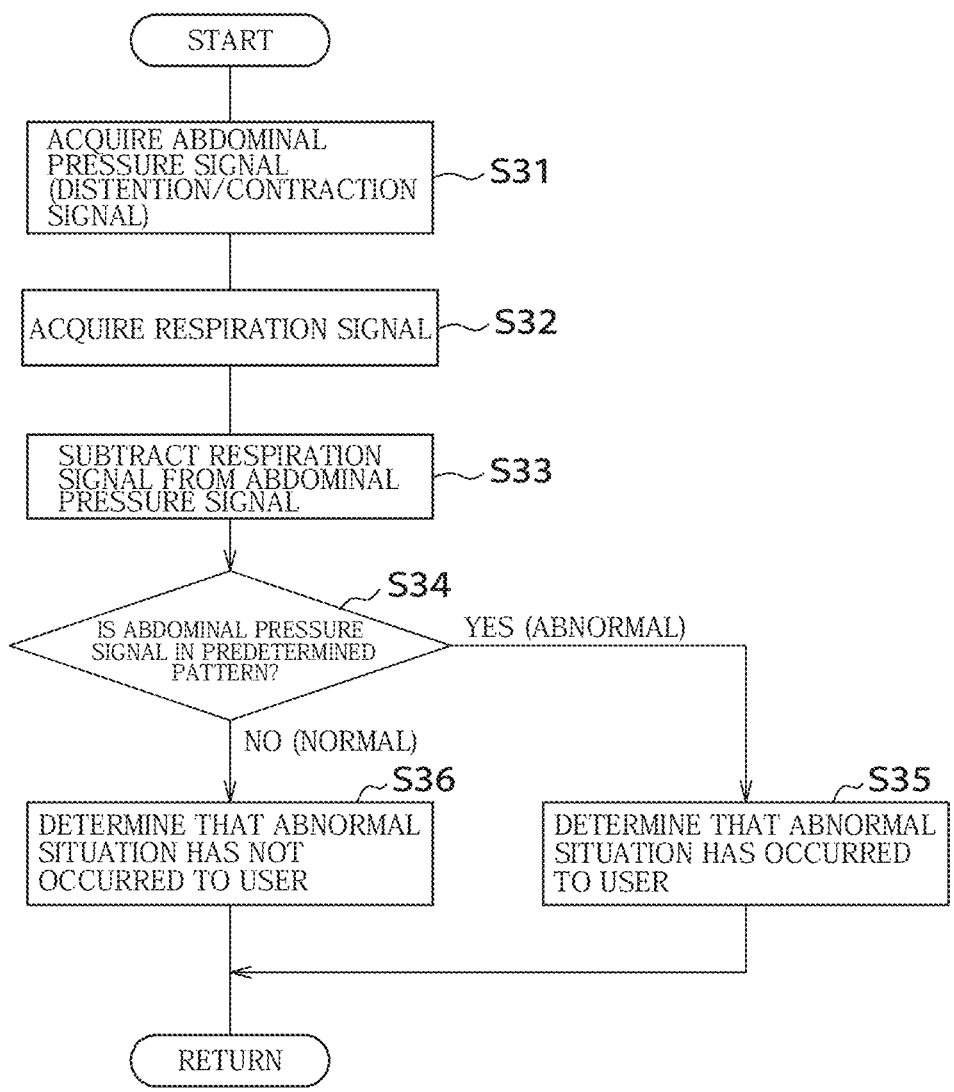
FIG. 6 is a flowchart showing an abdominal pressure abnormality determining processing by an abnormality determination unit of the communication terminal of the digital real security system according to the first embodiment of the present invention.

FIG. 6 is a flowchart showing an abdominal pressure abnormality determining processing by the abnormality determination unit 112 of the communication terminal 100, and is a subroutine of step S24 of FIG. 5.

First, in step S31, the abdominal pressure signal acquisition unit 101 acquires an abdominal pressure signal of the user's abdominal pressure sensor 10. This abdominal pressure signal is, for example, a distention/contraction signal according to abdominal distention and contraction.

In step S32, the abdominal pressure signal acquisition unit 101 acquires a respiration signal of the user's respiration sensor 20.

In step S33, the abdominal pressure signal extraction unit 102 regards an abdominal pressure signal as a signal and regards a respiration signal as noise, and subtracts the respiration signal from the acquired abdominal pressure signal. Specifically, the abdominal pressure signal extraction unit 102 subtracts, from a distention/contraction signal according to abdominal distention and contraction detected by the abdominal pressure sensor 10, a respiration signal component superimposed on said distention/contraction signal to acquire a distention/contraction signal with suppressed influence of respiration.

The abdominal pressure sensor 10 detects a distention/contraction signal according to abdominal distention and contraction. The present inventors have found, however, that the distention/contraction signal contains the influence of respiration as noise existing in a superimposed manner on a human quantitative change in length that is a person's intentional abdominal distention/contraction. Therefore, a person's intentional distention/contraction signal is acquired with the influence of respiration having been suppressed by subtracting a respiration signal detected by the respiration sensor 20 from a distention/contraction signal detected by the abdominal pressure sensor 10.

In step S34 onward, abnormality is determined using the distention/contraction signal from which the respiration signal has been subtracted by the abdominal pressure signal extraction unit 102. That is, a respiration signal is acquired separately from an abdominal pressure signal, and abnormality is determined based on a result of the abdominal pressure signal from which the respiration signal has been subtracted, regarding the respiration signal as noise.

The abnormality determination unit 112 determines in step S34 whether the abdominal pressure signal being a distention/contraction signal after subtracting of the respiration signal is consistent with that of a predetermined pattern determined in advance for reporting abnormality. If the distention/contraction signal after subtracting of the respiration signal is consistent with that of a predetermined pattern (YES in S34), it is judged to be abnormal to proceed to step S35.

If the distention/contraction signal after subtracting of the respiration signal is not consistent with that of a predetermined pattern (NO in S34), it is judged to be normal to proceed to step S36.

In step S35, the abnormality determination unit 112 determines that an abnormal situation has occurred to the user to return to step S24 of FIG. 5.

In step S36, the abnormality determination unit 112 determines that an abnormal situation in security has not occurred to the user to return to step S24 of FIG. 5.

Because the abnormality determination unit 112 determines abnormality of an object person under security based on the distention/contraction signal with suppressed influence of respiration, the respiration signal component that changes according to respiration is subtracted, only the person's intentional abdominal distention/contraction is accurately detected, and erroneous reports and failed reports are thus prevented to improve reliability, while only an abnormal situation in security of the user covered by the present system is determined.

[Report Control of Monitoring Device 200]ps <Report Example 1>

Figure 7:
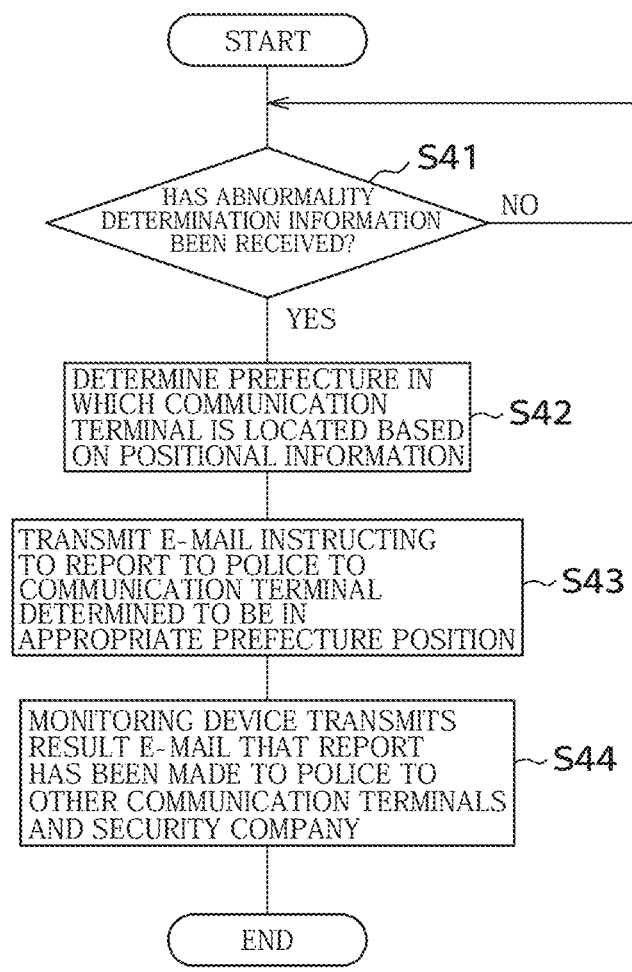
FIG. 7 is a flowchart showing a report control operation of the monitoring device of the digital real security system according to the first embodiment of the present invention.

FIG. 7 is a flowchart showing a report control operation of the monitoring device 200 of the digital real security system. The present flow is executed mainly by the control unit 201 (FIG. 1) of the monitoring device 200.

First, in step S41, the control unit 201 waits until the input unit 202 receives abnormality determination information by an e-mail message from the communication terminal 100. Alternatively, it may determine whether abnormality determination information and the latest positional information of the communication terminal 100 have been received. In the present embodiment, the communication terminal 100 is formed by a mobile phone, smartphone, or the like that is capable of mobile communications, and is used at the location (that is, existing position) of each individual. The monitoring device 200 receives normal notification every predetermined time (for example, one hour) to store the position of the communication terminal 100 in normal time where abnormality determination is not notified from the communication terminal 100.

If having received the abnormality determination information from the communication terminal 100, the control unit 201, based on the received positional information of the communication terminal 100, determines said communication terminal 100 is located in which of the prefectures being emergency police reporting telephone call receiving jurisdictional districts in step S42.

In step S43, the control unit 201 transmits an e-mail message instructing to report to a police 230 (refer to FIG. 1) preferentially to a communication terminal 100 determined to be existing in an appropriate prefecture being a jurisdictional district where the building under security exists.

In step S44, the control unit 201 of the monitoring device 200 transmits a result e-mail message that a report has been made to the police 230 to other communication terminals 100 and the security company 220 (refer to FIG. 1) to end the present flow. As above, the present report example 1 is of reporting preferentially to an information addressee that is in the same police administrative district as the user (victim).

In particular, the present report example 1 is only of reporting to other communication terminals 100, the security company 220, and the police 230, and is intentionally not of carrying out a warning, threat, or the like to the user's (victim's) communication terminal 100. That is, this is for safeguarding the user's (victim's) body without instigating the robber also in consideration of the case where the user (victim) is in such a dangerous situation that he/she cannot even use his/her voice. The present system has a unique effect of being able to reliably report an abnormal situation by the user's intention without the robber's awareness, and the present report example 1 can achieve maximum effect of the present system of reporting an abnormal situation without the robber's awareness.

<Report Example 2>

Report example 2 is an example of application to a building of service operations such as a store, bank, company office, station/air terminal, money exchanger, cash transport truck, bus, or taxi and an individual home (hereinafter, referred to a store or the like).

The above-described store or the like is installed with a plurality of surveillance cameras, and predetermined surveillance regions can be shot. Also, the surveillance cameras may follow a specific person or shooting location. Even if the surveillance cameras do not follow a shooting location, a person and the like can be shot from various angles by installing a plurality of the surveillance cameras.

A digital real security system in a store or the like will be described.

Figure 8:
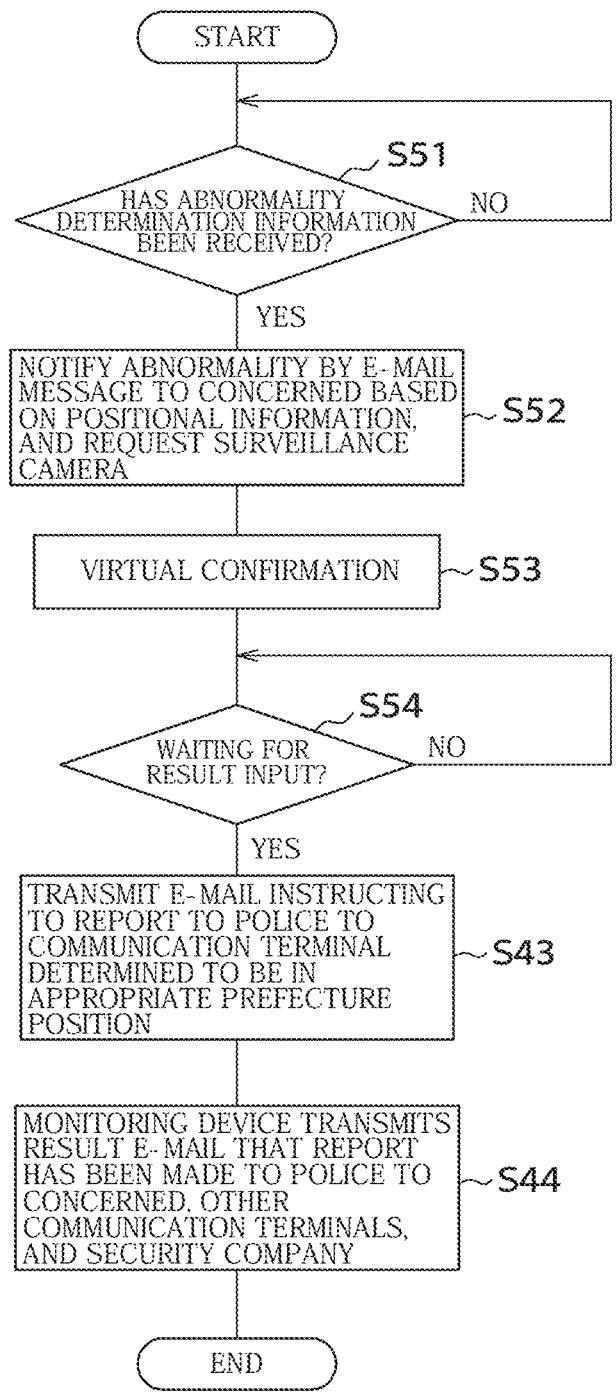
FIG. 8 is a flowchart showing a report control operation of the monitoring device of the digital real security system according to the first embodiment of the present invention.

FIG. 8 is a flowchart showing a report control operation of the monitoring device 200 of the digital real security system in a store or the like. The present flow is executed mainly by the control unit 201 (FIG. 1) of the monitoring device 200. The steps that perform the same processing as in FIG. 7 are denoted by the same reference numerals.

First, in step S51, the control unit 201 waits until the input unit 202 receives abnormality determination information by an e-mail message from the communication terminal 100.

If having received the abnormality determination information from the communication terminal 100, the control unit 201, based on the received positional information of the communication terminal 100, notifies the abnormality by an e-mail message to the store office, headquarters, security company, and the like being concerned, and requests to shoot a user concerned by the surveillance cameras in step S52. The store office, headquarters, security company, and the like, based on the user shooting request of the monitoring device 200, take a moving image of the user at the store concerned or the like by the surveillance cameras, and transmit the moving image to the monitoring device 200.

In step S53, the taken real-time moving image of the user is visually confirmed. In step S54, input of the visual confirmation result by the input unit 202 is waited for. As a result of the visual confirmation, if the abnormality is confirmed, the control unit 201 transmits an e-mail message instructing to report to a police 230 preferentially to a communication terminal 100 determined to be existing in an appropriate prefecture being a jurisdictional district where the building under security exists in step S43.

In step S44, the control unit 201 of the monitoring device 200 transmits a result e-mail message that a report has been made to the police 230 to the concerned, other communication terminals 100, and the security company 220 to end the present flow.

The present report example 2 is of safeguarding the user's (victim's) body without instigating the robber also in consideration of the case where the user (victim) is in such a dangerous situation that he/she cannot even use his/her voice. The present system is able to reliably report an abnormal situation by the user's intention without the robber's awareness. In particular, because the present report example 2 is of visually confirming a real-time moving image of an environment where the user exists while determining abnormality, a more reliable abnormal determination can be performed, and more appropriate measures can be implemented.

<Report Example 3>

By report examples 1 and 2, an abnormal situation can be reported without the robber's awareness. Report example 3 is an example of reporting an abnormal situation without the robber's awareness, followed by a threat to the robber.

Figure 9:
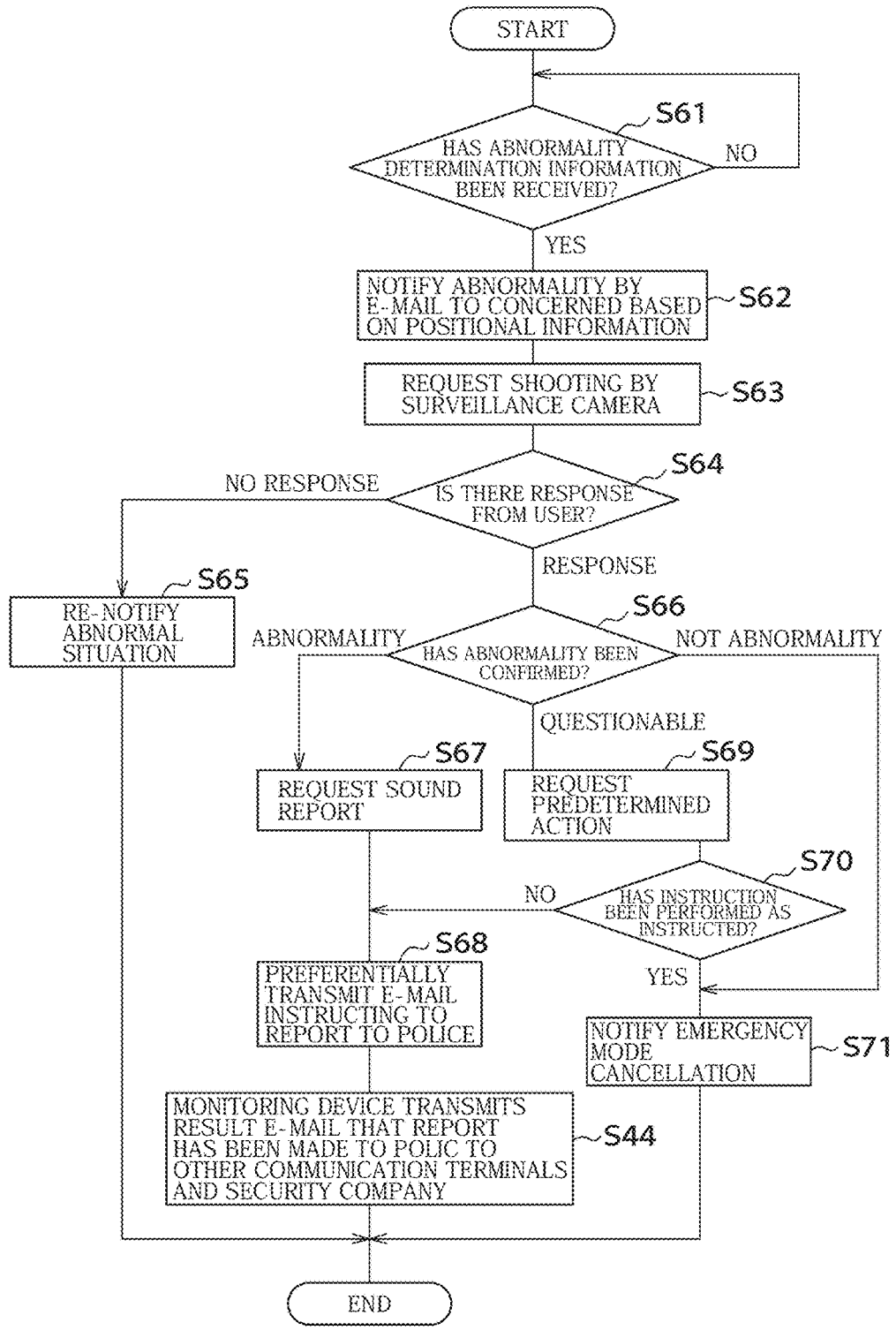
FIG. 9 is a flowchart showing a report control operation of the monitoring device of the digital real security system according to the first embodiment of the present invention.

FIG. 9 is a flowchart showing a report control operation of the monitoring device 200 of the digital real security system in a store or the like. The present flow is executed mainly by the control unit 201 (FIG. 1) of the monitoring device 200. The steps that perform the same processing as in FIG. 8 are denoted by the same reference numerals.

First, in step S61, the control unit 201 waits until the input unit 202 receives abnormality determination information by an e-mail message from the communication terminal 100.

If having received the abnormality determination information from the communication terminal 100, the control unit 201, based on the received positional information of the communication terminal 100, notifies the abnormality by an e-mail message to the store office, headquarters, security company, and the like being concerned, and causes the communication terminal 100 of the user to produce a sound to confirm the situation by an automated voice in step S62.

In step S63, the control unit 201 requests to shoot the user by the surveillance cameras. The store office, headquarters, security company, and the like, based on the user shooting request of the monitoring device 200, take a moving image of the user at the store or the like by the surveillance cameras, and transmit the moving image to the monitoring device 200.

In step S64, the control unit 201 determines whether there is a response from the communication terminal 100 of the user in response to the situation confirmation by an automated voice. If there is no response from the user's communication terminal 100, the control unit 201 re-notifies the emergency situation (abnormal situation) to the store or the like being concerned by attaching a photo(s) to an e-mail message in step S65.

If there is a response from the user's communication terminal 100, the real-time moving image of the user taken is visually confirmed to determine whether it is abnormality, questionable, or not abnormality in step S66. As a result of the visual confirmation, when it is abnormality, the control unit 201 requests the headquarters of the store or the like to make a sound report to an appropriate place in the store (a place in the store where the user is present) in step S67. The headquarters of the store or the like receives this request to make a threat toward the appropriate place in the store by sound notification (such as a threatening tone or a warning message).

In step S68, the control unit 201, after confirmation of the emergency situation by the headquarters of the store or the like and/or security company, based on the user's position, transmits an e-mail message instructing to report to a police 230 preferentially to a communication terminal 100 determined to be existing in an appropriate prefecture being a jurisdictional district where the building under security exists. In step S44, the control unit 201 of the monitoring device 200 transmits a result e-mail message that a report has been made to a police 230 to the concerned, other communication terminals 100, and the security company 220 to end the present flow.

As a result of the visual confirmation, if it is questionable, the control unit 201 requests the headquarters of the store or the like to cause the user to take a predetermined action (such as an action to inform that it is not an emergency situation) by a sound in step S69. The headquarters of the store or the like instructs the user to take an appropriate action by a voice message by receiving this request.

In step S70, the control unit 201, based on a response from the headquarters of the store or the like, determines whether the user has performed the action as instructed. If the user has performed the action as instructed, it is judged that it is not abnormality to proceed to step S71, and if the user has not performed the action as instructed, it is judged that it is abnormality to proceed to step S68.

If it is determined that it is not abnormality in the above-described step S66 or if the user has performed the action as instructed, the control unit 201 notifies the user and other communication terminals 100 in step S71 that the emergency mode has been cancelled to end the present flow.

As above, in the present report example 3, the headquarters office of a store having received an abnormal situation confirms a moving image of the surveillance cameras and threatens the robber, and can thereby prevent an incident. Also, the monitoring device 200 detects an abnormal situation, checks a moving image of the surveillance cameras, and threatens the intruder by a speaker. In such a situation that a third party is not involved in trouble, a repelling device (not shown) can be activated to repel the intruder.

<Report Example 4>

Similar to report example 3, report example 4 is an example of reporting an abnormal situation without the robber's awareness, followed by a threat to the robber.

Figure 10:
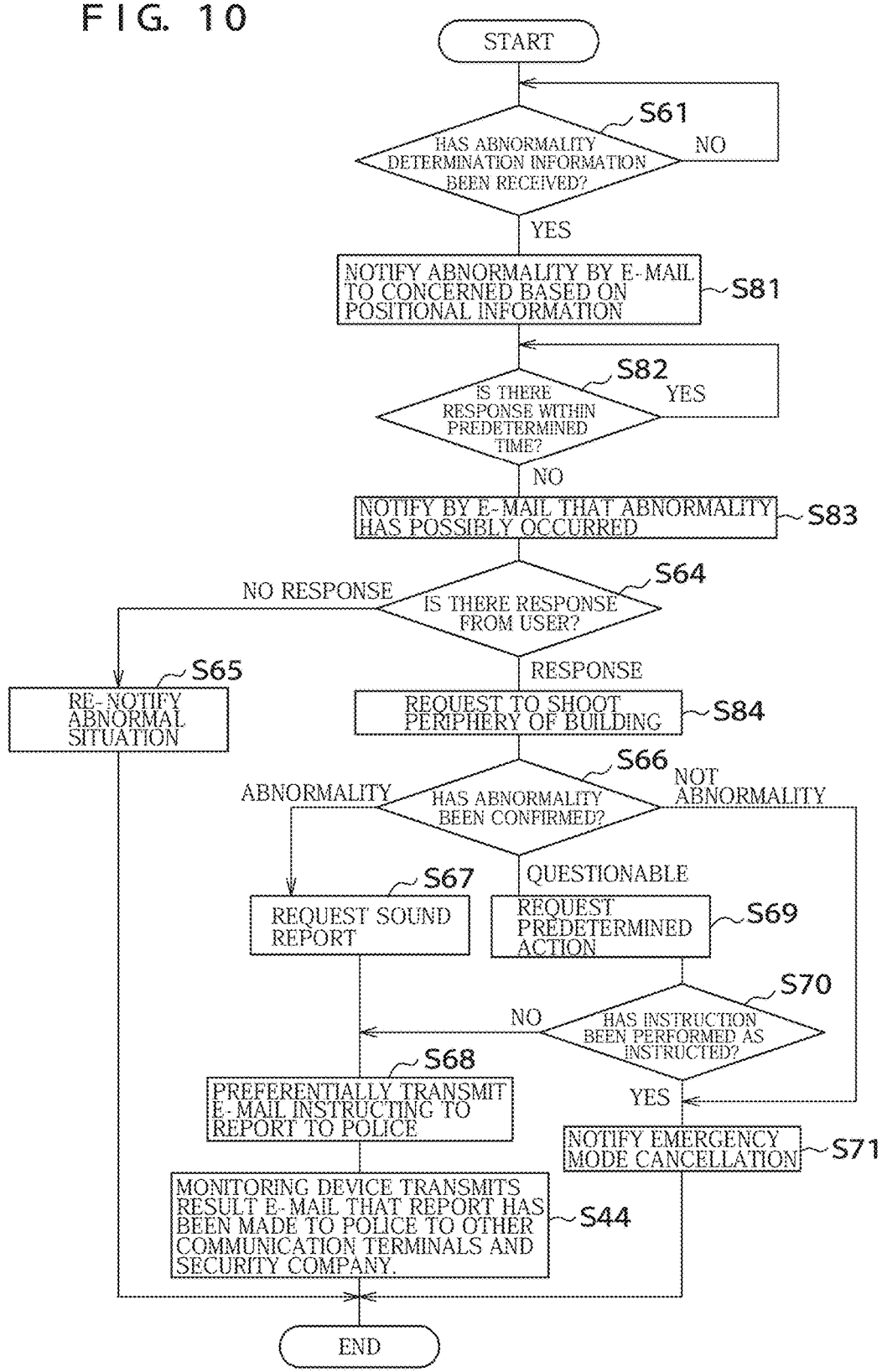
FIG. 10 is a flowchart showing a report control operation of the monitoring device of a corporation or individual of the digital real security system according to the first embodiment of the present invention.

FIG. 10 is a flowchart showing a report control operation of the monitoring device 200 of the digital real security system in a corporation or individual. The present flow is executed mainly by the control unit 201 (FIG. 1) of the monitoring device 200. The steps that perform the same processing as in FIG. 9 are denoted by the same reference numerals.

First, in step S61, the control unit 201 waits until the input unit 202 receives abnormality determination information by an e-mail message from the communication terminal 100.

If having received the abnormality determination information from the communication terminal 100, the control unit 201, based on the received positional information of the communication terminal 100, notifies the abnormality by an e-mail message to the family, security company, corporate headquarters, and/or the like being concerned, and causes the communication terminal 100 of the user to produce a sound to confirm the situation by an automated voice in step S81.

In step S82, the control unit 201 issues the above-described e-mail message to the family or corporate headquarters, and then determines whether there is a response to said e-mail message within a predetermined time (for example, three minutes). If there is no response within a predetermined time (for example, three minutes) even after the above-described e-mail message was issued, the control unit 201 notifies other users (other communication terminals 100) by an e-mail message that abnormality has possibly occurred to the user in step S83.

In step S64, the control unit 201 determines whether there is a response from the communication terminal 100 of the user in response to the situation confirmation by an automated voice. If there is no response from the user's communication terminal 100, the control unit 201 re-notifies the emergency situation to the store or the like being concerned by attaching a photo(s) to an e-mail message in step S65.

In step S84, the control unit 201 requests to shoot the periphery of the building by the surveillance cameras. The store office, headquarters, security company, and the like, based on the user shooting request of the monitoring device 200, take a moving image of the periphery of the building by the surveillance cameras, and transmit the moving image to the monitoring device 200.

In step S66, the real-time moving image of the user taken is visually confirmed to determine whether it is abnormality, questionable, or not abnormality.

As a result of the visual confirmation, if it is abnormality, the control unit 201 requests the headquarters of the store or the like to make a sound report to an appropriate place in the store (a place in the store where the user is present) in step S67. The headquarters of the store or the like receives this request to make a threat toward the appropriate place in the store by sound notification (such as a threatening tone or a warning message).

In step S68, the control unit 201, after confirmation of the emergency situation by the headquarters of the store or the like and/or security company, based on the user's position, transmits an e-mail message instructing to report to a police 230 preferentially to a communication terminal 100 determined to be existing in an appropriate prefecture being a jurisdictional district where the building under security exists.

In step S44, the control unit 201 of the monitoring device 200 transmits a result e-mail message that a report has been made to the police 230 to the concerned, other communication terminals 100, and the security company 220 to end the present flow.

As a result of the visual confirmation, if it is questionable, the control unit 201 requests the headquarters of the store or the like to cause the user to take a predetermined action (such as an action to inform that it is not an emergency situation) by a sound in step S69. The headquarters of the store or the like receives this request, and instructs the user to take an appropriate action by a voice message.

In step S70, the control unit 201, based on a response from the headquarters of the store or the like, determines whether the user has performed the action as instructed. If the user has performed the action as instructed, it is judged that it is not abnormality to proceed to step S71, and if the user has not performed the action as instructed, it is judged that it is abnormality to proceed to step S68.

If it is determined that it is not abnormality in the above-described step S66 or if the user has performed the action as instructed, the control unit 201 notifies the user and other communication terminals 100 in step S71 that the emergency mode has been cancelled to end the present flow.

As above, even in a situation where an employee(s) is threatened by a threatener and cannot take any actions, the monitoring device 200 can report the abnormal situation to the office and headquarters of the store and the security company 220 to call the emergency number 110 (i.e., make an emergency call) to a police 230 in real time, without the threatener's awareness.

As described above in detail, according to the present embodiment, the digital real security system comprises the abdominal pressure signal acquisition unit 101 that acquires an abdominal pressure signal from the abdominal pressure sensor 10 for detecting a user's abdominal pressure and acquires a respiration signal from the respiration sensor 20 for detecting the user's breathing, the abdominal pressure signal extraction unit 102 that subtracts the respiration signal component from the acquired abdominal pressure signal to extract an abdominal pressure signal with suppressed influence of respiration, the abnormality determination unit 112 that determines the user's abnormality based on the abdominal pressure signal from which the respiration signal component has been subtracted, and the alarm sending unit 203 that reports an abnormal situation based on a determination result as being the occurrence of an abnormal situation.

To the abnormality determination unit 112, an abdominal pressure signal extracted by the abdominal pressure signal extraction unit 102 is repeatedly transmitted. When the abdominal pressure signal indicates an abnormal situation, it is determined that an abnormal situation has occurred.

That is, an abdominal pressure is detected, breathing is detected separately therefrom, and abnormality is determined based on a result of the abdominal pressure signal from which the respiration signal has been subtracted, regarding the breathing as noise.

According to this configuration, the respiration signal component that changes according to respiration is subtracted and only the person's intentional abdominal pressure is accurately detected, which thus prevents erroneous reports and failed reports to improve reliability, while allowing the victim to reliably report the occurrence of an emergency situation. Also, this configuration allows reliably reporting an abnormal situation by the user's intention without the robber's awareness.

For example, a user can, even in a situation where he/she is threatened by a threatener (robber) and cannot take any actions, report the abnormal situation to his/her family (other communication terminal(s) 100), the office and headquarters of the store and the security company 220 by changing from normal time such as changing his/her abdominal pressure pattern, without the threatener's awareness. The family or the like can make confirmation and call the emergency number 110 to a police 230 to prevent trouble or an incident.

Also, similarly for an employee(s) of a cash transport truck, bus, taxi, precious metal, a jewelry counter, or the like, the safety of the employee can be ensured to protect him/her against a robbery case. Also, even for the aged, children, and those said to have health problems being socially vulnerable and even from a remote place, a support action for help can be provided in real time on the occurrence of an abnormal situation. As a result, the life and property of a corporation or individual employee(s) can be protected in real time, let alone a family, and the digital real security system is useful as a system for countermeasures against crime, and its economic advantages and contribution are considerably great.

For example, in the case where a robber intrudes into a building of service operations such as a store, bank, company office, station/air terminal, money exchanger, cash transport truck, bus, or taxi and an individual home, its employee can reliably report the abnormal situation by distending and contracting his/her abdomen so as to become consistent with a predetermined abdominal pressure pattern, and his/her family concerned can call the emergency number 110 to the police.

Also, when the abdominal pressure sensor 10 stops due to a threatener (robber)'s violence or the communication terminal 100 is robbed by a robber and signal communications between the abdominal pressure sensor 10 and the communication terminal 100 are not available, the communication terminal 100 transmits the current position identified by the GPS and that the user is in an emergency to the monitoring device 200, and the monitoring device 200 reports the same further to his/her corporate or family concerned person in real time, which allows the corporate or family concerned person to call the emergency number 110 to the police. As above, even when in a situation where an employee(s) is threatened by a threatener and cannot take any actions, the monitoring device 200 is capable of reporting the abnormal situation to the headquarters office of the store and the security company 220 to allow calling the emergency number 110 to a police 230 in real time, without the threatener's awareness.

In the present embodiment, because a report is made preferentially to an information addressee that is in the same police administrative district as the victim, the person having received the report can promptly make an emergency call to the police of the police administrative district where the victim is.

Here, in order to increase the accuracy of abnormality sensing by the abdominal pressure sensor 10, the same determining method may be repeated or different determining methods may be combined to finally determine it to be abnormal when it is determined to be abnormal in all those cases.

(Second Embodiment)

A second embodiment of the present invention is an example of application to a user, cash transport truck, bus, taxi, or the like. The digital real security system according to the second embodiment of the present invention has the same hardware configuration as in FIG. 1, and therefore, description thereof will be omitted.

Next, a registration processing of the monitoring device 200 of the digital real security system will be described.

Figure 11:
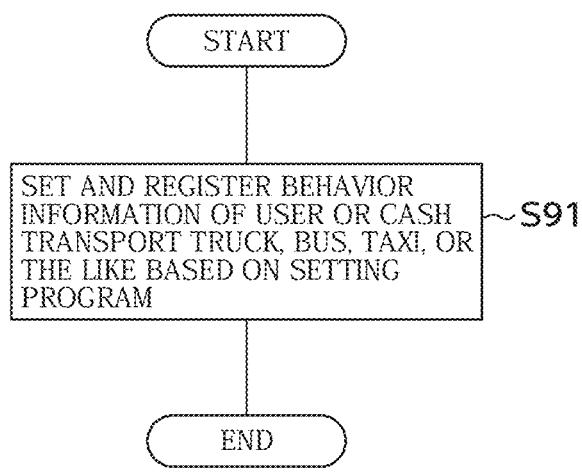
FIG. 11 is a flowchart showing a registration processing of the monitoring device of the digital real security system according to the first embodiment of the present invention.

FIG. 11 is a flowchart showing a registration processing of the monitoring device 200 (FIG. 1). The present flow is executed mainly by the control unit 201 of the monitoring device 200.

In step S91, the control unit 201 registers behavior information of a user of a cash transport truck, bus, taxi, or the like, in advance, as monitoring device registration setting information (not shown). As the monitoring device registration setting information, user information of the abdominal pressure sensor 10 correlated with the communication terminal 100, the mobile phone number of the communication terminal, the name, a password, a contact address, normal-time abdominal pressure information, etc., are registered. Also, an abdominal pressure pattern program is registered.

FIG. 12 is a flowchart showing a behavior monitoring control operation of the monitoring device 200 of the digital real security system. The present flow is executed mainly by the control unit 201 (FIG. 1) of the monitoring device 200.

First, if the user is a user of a cash transport truck, bus, taxi, or the like, the control unit 201 sets the mode setting of the communication terminal 100 to a behavior monitoring mode in step S101. Also, the mode setting of the communication terminal 100 is also similarly set to a behavior monitoring mode. In this case, there may be a mode of the communication terminal 100 first being set to a behavior monitoring mode and reporting its behavior monitoring mode to the monitoring device 200, and the monitoring device 200 then setting a behavior monitoring mode.

In step S102, the control unit 201 acquires positional information of the communication terminal 100 transmitted from the communication terminal 100, for example, every 30 minutes. Here, it is preferable that notification of positional information by the GPS in the present embodiment is every predetermined time (for example, 30 minutes) shorter than the predetermined time (for example, one hour) of the first embodiment. That is, the user (communication terminal 100) of a cash transport truck, bus, taxi, or the like possibly moves in the vehicle, and it is considered that the positional information greatly changes in this case. It is therefore preferable to acquire positional information every time shorter than the predetermined time of the first embodiment.

Also, positional information can be continuously acquired by an autonomous navigation system using a gyroscope etc., even when the communication terminal 100 is in a place where radio communication is not available such as the inside of a tunnel. Further, when the communication terminal 100 is thus in a place where radio communication is not available, the monitoring device 200 can no longer receive the position of the communication terminal 100, but an erroneous report can be prevented, when it is assumed that the communication terminal 100 is in an area where radio communication is not available on a map, by judging that even a failure in acquiring positional information is not abnormality.

In step S103, the control unit 201 monitors a set behavior program and positional information of the user of a cash transport truck, bus, taxi, or the like at all times (here, monitors every 30 minutes). In step S104, the control unit 201 determines whether a predetermined time (for example, 30 minutes or more) has elapsed with a mismatch between the set behavior program and the positional information by the GPS of the user of a cash transport truck, bus, taxi, or the like.

If the predetermined time has not elapsed with a mismatch between the set behavior program and the positional information by the GPS, it is judged that the set behavior program and the positional information are matching in behavior to return to the above-described step S102. If the predetermined time has elapsed with a mismatch between the set behavior program and the positional information by the GPS, it is judged there is a mismatch in behavior between the set behavior program and the positional information to proceed to step S105. In step S105, the control unit 201 determines whether notification of the occurrence of an abnormal situation from the user (communication terminal 100) of a cash transport truck, bus, taxi, or the like has been received. In addition, the determination of an abnormal situation has been described according to FIG. 5.

If notification of the occurrence of an abnormal situation has been received, the control unit 201 sends an alarm by an e-mail message or sound to the user's communication terminal 100 via the alarm sending unit 203 (FIG. 1) in step S106, and transmits an e-mail message to the user's family, corporate headquarters, and the like. If notification of the occurrence of an abnormal situation has not been received, the control unit 201 returns to the above-described step S102.

In step S107, the control unit 201 determines whether there is a response from the user's communication terminal 100.

If there is a response from the user's communication terminal 100, the control unit 201 returns to the above-described step S102. On the other hand, if there is no response from the user's communication terminal 100, the control unit 201 continues monitoring of the positional information by the GPS of the user's communication terminal 100 in step S108.

In step S109, the control unit 201 determines whether a predetermined time (for example, 30 minutes or more) has elapsed with a mismatch in behavior between the set behavior program and the positional information.

If the predetermined time has not elapsed with a mismatch between the set behavior program and the positional information by the GPS, it is judged that the set behavior program and the positional information are matching in behavior to return to the above-described step S102. If the predetermined time has elapsed with a mismatch between the set behavior program and the positional information by the GPS, it is judged there is a mismatch in behavior between the set behavior program and the positional information to proceed to step S110. In step S110, the control unit 201, by the headquarters and/or security company, confirms the emergency situation, confirms the user's position, and calls the emergency number 110 to the police to end the present flow.

Here, as an example of a reporting method, as in the first embodiment, a report may be made preferentially to an information addressee that is in the same police administrative district as the victim.

As above, according to the present embodiment, even when a threatener (robber) attacks a cash transport truck, bus, taxi, or the like and threatens its employee and the employee is restrained and cannot take any actions or call for help, the employee can reliably report the occurrence of an abnormal situation together with current positional information. Also, even when the headquarters contacts the employee by telephone if there is any abnormality and hears from the employee that he/she is safe, the headquarters can call the emergency number 110 to the police if the behavior of the cash transport truck, bus, taxi, or the like confirmed by the GPS is not of behaving along a prescribed course, so that an incident can be prevented. Further, a moving image or photo(s) of a surveillance camera installed inside the vehicle of the cash transport truck, bus, taxi, or the like is transmitted by e-mail to a concerned person at the corporate headquarters to convey the abnormal state of the cash transport truck, bus, taxi, or the like. The concerned person at the corporate headquarters having received the e-mail confirms the situation inside the vehicle, and if it is an emergency situation, calls the emergency number 110 to the police, and is thereafter capable of responding thereto by tracking the cash transfer truck, bus, taxi, or the like by the GPS and mobile terminal.

(Third Embodiment)

A third embodiment of the present invention is an example of reporting in a distinguishing manner different abnormal situations different by different abdominal pressure patterns. The digital real security system according to the present embodiment has the same hardware configuration as in FIG. 1, and therefore, description thereof will be omitted. In the present embodiment, the storage unit 105 of FIG. 1 stores abdominal pressure patterns shown in FIG. 13.

FIG. 13 is a chart showing an example of abdominal pressure patterns of the digital real security system according to the present embodiment.

As shown in FIG. 13, each user has a normal abdominal pressure and abnormal states [i. Attention, ii. Abnormal situation, iii. Emergency state] as the abdominal pressure patterns of the present embodiment.

For example, user A sets a I pattern in which approximately two times of distention and contraction is performed within ten seconds for the "i. Attention," a II pattern of five times for the "ii. Abnormal situation," and a III pattern of ten times for the "iii. Emergency state," according to the personal level. The abdominal pressure patterns are created by stopping the above-described "i," "ii," or "iii" one time or two to three times by repetition at intervals set depending on the on-site situation. Also, it is preferable to create abdominal pressure pattern programs by user's industry and/or by categories of children, minors, adults, and the aged.

As above, according to the present embodiment, storing in advance a plurality of different abdominal pressure patterns allows, in response to the occurrence of various abnormal situations, determining the respective abnormal situations in a distinguishing manner to make reports.

(Fourth Embodiment)

In the first to third embodiments, a person's intentional distention/contraction signal is acquired with the influence of respiration having been suppressed by subtracting a respiration signal detected by the respiration sensor 20 from a distention/contraction signal detected by the abdominal pressure sensor 10. The first to third embodiment are however absolutely premised on a user wearing (using) the abdominal pressure sensor 10 and the respiration sensor 20, and based thereon the person's intentional distention/contraction signal is acquired. That is, using the abdominal pressure sensor 10 and the respiration sensor 20 at the same time is for increasing the reliability of a distention/contraction signal.

However, what will happen if a thug robs the user of the present sensor and moreover wears the present sensor? In this case, because the present sensor itself is worn on the thug and then operating, abnormality due to an operation stop of the present sensor cannot be determined. Also, using the abdominal pressure sensor 10 and the respiration sensor 20 at the same time can increase the reliability of a distention/contraction signal but does not allow distinguishing whether the signal comes from the user or thug. Then, a report will be made by the way of breathing using the respiration sensor 20, but this is originally a method for the user reporting without the thug's awareness. Therefore, it cannot be used if the present sensor is robbed by the thug. Moreover, if the thug leaves the present sensor as it is, there is a possibility that the occurrence of abnormality can be sensed by a judgment of the situation such as the absence of a response to a regular transmission or a call. However, as described above, it is difficult to determine abnormality if the thug robs the user of the present sensor and then wears the present sensor.

The fourth embodiment of the present invention is an example of enabling reporting an abnormal situation even when a thug robs the user of the present sensor and wears the same.

The digital real security system according to the present embodiment has the same hardware configuration as in FIG. 1, and therefore, description thereof will be omitted. In the present embodiment, the storage unit 105 of FIG. 1 stores normal-time abdominal pressure patterns and numbers of breathing times per unit time of object persons under security in correlation with the respective object persons under security. Also, the abnormality determination unit 112 of FIG. 1 verifies the normal-time numbers of breathing times/abdominal pressure patterns of object persons under security stored in the storage unit 105 by matching to a normal-time number of breathing times/abdominal pressure pattern of a wearer of the present sensor acquired this time to determine abnormality.

Figure 14:
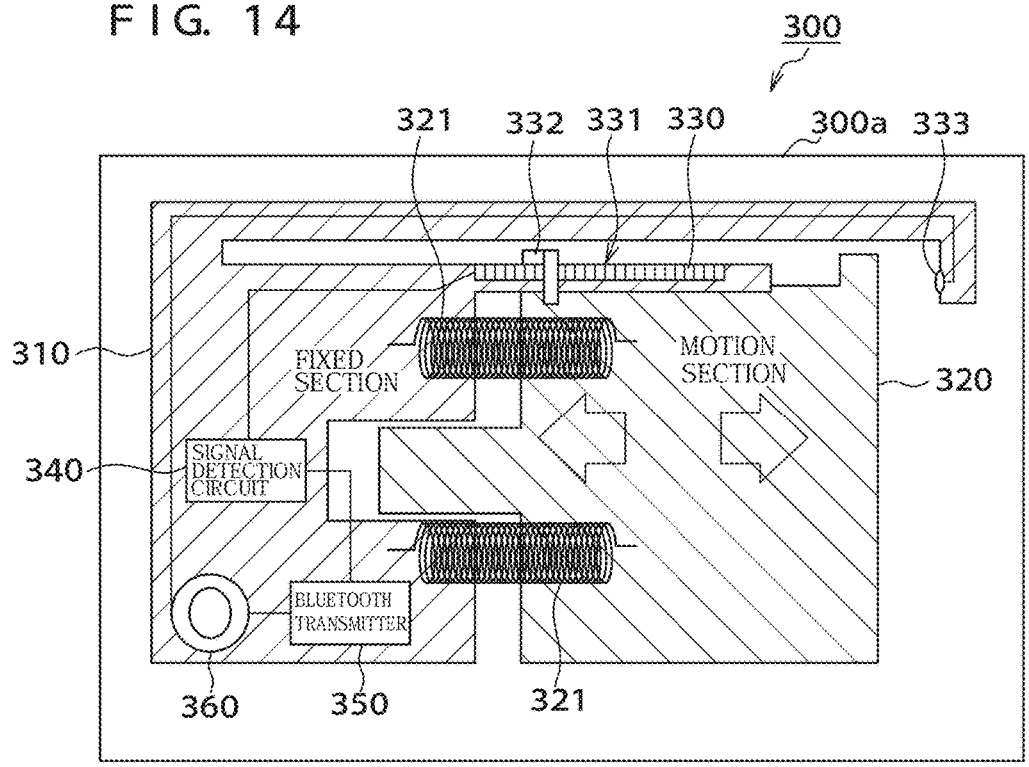
FIG. 14 is a schematic view showing a configuration of a chest/abdominal motion signal detection device of a digital real security system according to a fourth embodiment of the present invention.
Figure 15:
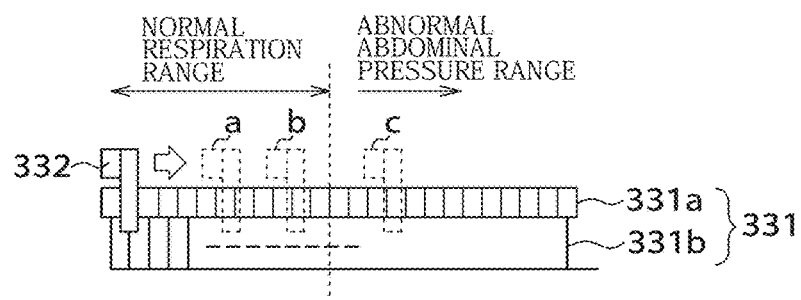
FIG. 15 is a main part enlarged view of a motion position sensor of FIG. 14.

FIG. 14 is a schematic view showing a configuration of a chest/abdominal motion signal detection device 300. FIG. 15 is a main part enlarged view of a motion position sensor of FIG. 14. The chest/abdominal motion signal detection device 300 of FIG. 14 shows a specific example of the abdominal pressure sensor 10 of FIG. 1. Also, as a means of communication between the chest/abdominal motion signal detection device 300 of FIG. 14 and the communication terminal of FIG. 1, the case of being Bluetooth (registered trademark) is taken as an example. In addition, the means of communication may be another wireless communication system such as Wi-Fi radio or specified low power radio or a wire connection by an interface such as a USB.

As shown in FIG. 14, the chest/abdominal motion signal detection device 300 comprises in a main body 300*a* a fixed section 310 that serves as a reference of motion and a motion section 320 in a substantially rectangular shape that moves due to an abdominal pressure with respect to the fixed section 310, two springs 321 that bias the motion section 320 toward the fixed section 310, a sensor unit 330 in a long shape that is present on the fixed section 310 and disposed so as to extend along a side surface of the motion section 320 and senses motion positions of the motion section 320 in a tensile direction by the abdominal pressure and a direction opposite thereto, a signal detection circuit 340 that processes the signal sensed by the sensor unit 330 to detect an abdominal pressure signal, a Bluetooth transmitter 350 that transmits the detected abdominal pressure signal to the communication terminal 100 (refer to FIG. 1), and a power supply unit 360 consisting of a button cell or the like that supplies electrical power to the respective units. In addition, the motion section 320 moves within an appropriate range due to a guide (not shown).

The fixed section 310 and the motion section 320 are fitted to, for example, a belt that is wound around the abdomen so that the distance therebetween changes due to a change in abdominal pressure.

The sensor unit 330 is composed of a motion position sensor 331 in a long shape that is present on the fixed section 310 and disposed so as to extend along a side surface of the motion section 320 and a movable piece 332 that is present on the motion section 320 and projects from the motion section 320 toward the motion position sensor 331, and slides out of contact with an upper surface of the motion position sensor 331. The movable piece 332 is fixed to the motion section 320, and slides over the upper surface of the motion position sensor 331 in conjunction with the movement of the motion section 320.

As shown in FIG. 15, the motion position sensor 331 consists of a plurality of detection sensors 331a disposed in a defined manner in a long shape, and signal lines 331b from the respective detection sensors 331a are connected to the signal detection circuit 340. In the present embodiment, photoelectric sensors are used as the detection sensors 331a. As a result of the movable piece 332 that is in conjunction with the motion section 320 blocking any detection sensor 331a out of the detection sensors 331a from receiving light, the detection sensor 331a detects a change in the amount of light received. Because the disposition of the respective detection sensors 331a corresponds to motion positions of the abdominal pressure, motion position information of the abdominal pressure can be acquired based on a change in the amount of light received by the detection sensor concerned.

As shown by reference signs a, b, and c of FIG. 15, the movable piece 332 can move the respective detection sensors 331a to the left and right along with motions of the motion section 320. Reference signs a and b of FIG. 15 show examples where the movable piece 332 is in a normal respiration range, and reference sign c of FIG. 15 shows an example where the movable piece 332 is in an abnormal abdominal pressure range.

In addition, providing a photo coupler configuration of a light emitting element (such as an LED) provided on the movable piece side and a light receiving element provided on the detection sensor side allows further increasing detection accuracy. Also, as another example of the non-contact sensor, it is also possible to use a magnetic material for the side of the movable piece 332 and use Hall elements for the respective detection sensors 331a so as to detect the position of the movable piece 332 based on a change in magnetic field. Further, as a simple configuration, the sensor unit 330 may be a contact sensor. The contact sensor can be realized using, for example, a conductive movable piece connected to the signal detection circuit 340 and conductive pads as the respective detection sensors. In this case, the conductive movable piece slides in contact with an upper surface of the conductive pads, motion position information of the abdominal pressure can be acquired depending on contact positions with the respective detection sensors (conductive pads).

In the configuration described above, a description is given, as the chest/abdominal motion signal detection device 300, of an example of being fitted to a belt and attached to a user's chest and abdomen so as to acquire numerical motion values of the chest and abdomen, but the chest/abdominal motion signal detection device 300 may only be attached to the abdomen. In this state, the motion section 320 is biased toward the fixed section being in the direction of the right facing arrow of FIG. 14 by a contracting force of the springs 321. The motion section 320 then moves in the direction of the right facing arrow of FIG. 14 by tension due to the user's abdominal pressure. The sensor unit 330 detects the left and right moving states by the motion section 320 as changes in the amount of received light by which the movable piece 332 blocks the respective detection sensors 331a from receiving light. The signal detection circuit 340, based on a change in the amount of light received by a detection sensor, detects motion position information (an abdominal pressure signal) of the detection sensor concerned. The Bluetooth transmitter 350 transmits the detected abdominal pressure signal to the communication terminal 100 (FIG. 1).

FIG. 16(A) and FIG. 16(B) are charts each showing an example of chest/abdominal motion numerical settings in user's normal respiration time.

As users' normal-time abdominal pressure patterns, the lengths around the chest and around the abdomen when the user inhales (a: breathe in) and exhales (b: breathe out) can be set as numerical motion values in correlation with the respective users. Along therewith, the numbers of breathing times per unit time can also be set in correlation with the respective users. Specifically, for example, numerical motion values of a predetermined number of breathing times (for example, 20 times) in normal respiration time or numerical motion values for a predetermined time (for example, for one minute) are detected. FIG. 16(A) shows the numerical motion values of the chest and abdomen and the number of breathing times of one minute's normal respiration. Similarly, numerical motion values of a predetermined number of breathing times (for example, 20 times) in normal respiration time or numerical motion values for a predetermined time (for example, for one minute) are detected as the same user's 30-minutes-later update settings. FIG. 16(B) shows as the 30-minutes-later update settings the numerical motion values of the chest and abdomen and the number of breathing times of one minute's normal respiration. As can be understood by a comparison of FIG. 16(A) with FIG. 16(B), there are variations depending on time even with the same user. Therefore, in the present embodiment, predetermined margins are provided in advance using the variations as allowances.

Hereinafter, the operation of the digital real security system using the chest/abdominal motion signal detection device 300 configured as described above will be described.

For the digital real security system of the present embodiment, similar to the registration processing (FIG. 3) of the first embodiment, the following registration has been executed beforehand by the registration unit 111 (FIG. 1) of the control unit 110 of the communication terminal 100.

The control unit 201 (FIG. 1) registers user information transmitted from the communication terminal 100, in advance, as monitoring device registration setting information (not shown). Here, the monitoring device registration setting information are user information of the chest/abdominal motion signal detection device 300 and the respiration sensor 20 correlated with the communication terminal 100, the mobile phone number of the communication terminal, the name, a password, a contact address, normal-time respiratory information, etc.

Also, the control unit 201 of the monitoring device 200 registers an abdominal pressure pattern program representing an abdominal pressure pattern. The abdominal pressure pattern program is based on the chest/abdominal motion numerical settings in normal respiration time of FIG. 16. Particularly, the storage unit 105 (FIG. 1) has stored normal numbers of breathing times/abdominal pressure patterns of object persons under security.

[Abnormality Determining Processing]

FIG. 17 is a flowchart showing an abdominal pressure abnormality determining processing by the abnormality determination unit 112 of the communication terminal 100, and is a subroutine of step S24 of FIG. 5. The flow is different in content from that of FIG. 6, but the flow shown in the drawing is the same.

First, in step S131, the abdominal pressure signal acquisition unit 101 acquires an abdominal pressure signal of the user's chest/abdominal motion signal detection device 300. This abdominal pressure signal is, for example, a distention/contraction signal according to abdominal distention and contraction.

In step S132, the abdominal pressure signal acquisition unit 101 acquires a respiration signal of the user's respiration sensor 20.

In step S133, the abdominal pressure signal extraction unit 102 regards an abdominal pressure signal as a signal and regards a respiration signal as noise, and subtracts the respiration signal from the acquired abdominal pressure signal. Specifically, the abdominal pressure signal extraction unit 102 subtracts, from a distention/contraction signal according to abdominal distention and contraction detected by the abdominal pressure sensor 10, a respiration signal component superimposed on said distention/contraction signal to acquire a distention/contraction signal with suppressed influence of respiration.

The chest/abdominal motion signal detection device 300 detects a distention/contraction signal according to abdominal distention and contraction. Here, a person's intentional distention/contraction signal is acquired with the influence of respiration having been suppressed by subtracting a respiration signal detected by the respiration sensor 20 from a distention/contraction signal detected by the chest/abdominal motion signal detection device 300.

In step S134 onward, abnormality is determined using the distention/contraction signal from which the respiration signal has been subtracted by the abdominal pressure signal extraction unit 102. That is, a respiration signal is acquired separately from an abdominal pressure signal, and abnormality is determined based on a result of the abdominal pressure signal from which the respiration signal has been subtracted, regarding the respiration signal as noise.

The abnormality determination unit 112 determines in step S134 whether the abdominal pressure signal being a distention/contraction signal after subtracting of the respiration signal is consistent with that of a predetermined pattern determined in advance for reporting abnormality.

Further, the abnormality determination unit 112 verifies the normal numbers of breathing times/abdominal pressure patterns of object persons under security stored in the storage unit 105 (FIG. 1) by matching to a normal number of breathing times/abdominal pressure pattern of the wearer of the present sensor acquired this time.

If the distention/contraction signal after subtracting of the respiration signal is consistent with that of a predetermined pattern and moreover, if the matching verification result of the normal numbers of breathing times/abdominal pressure patterns of object persons under security is a mismatch (YES in S134), it is judged to be abnormal to proceed to step S135.

If the distention/contraction signal after subtracting of the respiration signal is not consistent with that of a predetermined pattern and the matching verification result of the normal numbers of breathing times/abdominal pressure patterns of object persons under security is a match (NO in S134), it is judged to be normal to proceed to step S136.

In step S135, the abnormality determination unit 112 determines that an abnormal situation has occurred to the user to return to step S24 of FIG. 5.

In step S136, the abnormality determination unit 112 determines that an abnormal situation in security has not occurred to the user to return to step S24 of FIG. 5.

Because the abnormality determination unit 112 determines abnormality of an object person under security based on the distention/contraction signal with suppressed influence of respiration, the respiration signal component that changes according to respiration is subtracted, only the person's intentional abdominal distention/contraction is accurately detected, and erroneous reports and failed reports are thus prevented to improve reliability, while only an abnormal situation in security of the user covered by the present system is determined.

As above, in the present embodiment, the chest/abdominal motion signal detection device 300 that detects a number of breathing times and abdominal pressure pattern of personnel to which the same is fitted and the storage unit 105 that stores a user's number of breathing times and abdominal pressure pattern detected by the chest/abdominal motion signal detection device 300 are provided, and the abnormality determination unit 112 matches the number of breathing times and abdominal pressure pattern detected by the chest/abdominal motion signal detection device 300 to the user's number of breathing times and abdominal pressure pattern stored in the storage unit 105, and determines whether it is abnormality based on the match result, which therefore enables matching verification even when a thug robs the user of the chest/abdominal motion signal detection device 300 and wears the same, to allow determining an abnormal situation so as to allow reporting the abnormal situation.

The above description is an exemplification of preferred embodiments of the present invention, and the scope of the present invention is not limited thereto. A belt with the chest/abdominal motion signal detection device 300 fitted may be wound around both the chest and abdomen, or may be wound around only one of the chest and abdomen. When the belt is wound around the chest, the pattern called an abdominal pressure pattern of course means a chest pattern in actuality. Also, the matching may be by matching both of the number of breathing times and abdominal pressure pattern, or may be by matching only one of the number of breathing times and abdominal pressure pattern. For the abdominal pressure pattern matching, a common pattern matching technique can be used. Therefore, the matching may be by, for example, a comparison of the lengths around the abdomen. Also, for example, in the present embodiment, a description has been given of the case of using the telephone line 210 as a public line, but the present invention is not limited to this case, and for example, a radio communication line, the Internet, or a LAN may be used as a public line. Moreover, the communication terminal may be used according to the type of the public line, such as a transceiver used as a communication terminal when the public line is radio communication, and a personal computer or a palmtop computer used as a communication terminal when the public line is the Internet or a LAN. Thus constructing a digital real security system using an existing public line allows expanding the usage form of a digital real security system and allows suppressing the construction costs of a digital real security system.

Moreover, the title of a digital real security system and method has been used in the present embodiment, but this is for convenience of description, and the title may be digital real security, a crime-prevention system, a security method, or the like. Further, detection of an abnormal situation covers all of publicly-known matters. Examples of the abnormal situation are intrusion or approach of a suspicious person(s). Also, the report may be any, without being limited to an e-mail message.

Also, a digital real security system and method of the present invention can also be realized by a program to operate a computer as the present digital real security system or method. This program may be stored in a storage medium that can be read by a computer.

This storage medium recorded with the program may be a ROM itself of the present digital real security system, or may be a storage medium such as a CD-ROM that can be read, when a program reading device such as a CD-ROM drive is provided as an external storage device, by inserting therein the storage medium.

Moreover, the above-described storage medium may be a magnetic tape, a cassette tape, a flexible disk, a hard disk, an MO/MD/DVD or the like, or a semiconductor memory.

All publications, patents and patent applications cited in the present specification are hereby incorporated by reference in their entirety.

INDUSTRIAL APPLICABILITY

The digital real security system and method according to the present invention provide real-time responses in corporate and commercial facilities, offices, and the like to prevent losses of property and life and economic losses, whereby providing great utilization effects.

REFERENCE SIGNS LIST

10 Abdominal pressure sensor
20 Respiration sensor
100 Communication terminal
101 Abdominal pressure signal acquisition unit
102 Abdominal pressure signal extraction unit
103 GPS function unit
104 Communication unit
105 Storage unit (storage means)
110, 201 Control unit
111 Registration unit
112 Abnormality determination unit (abnormality determining means)
200 Monitoring device
201 Control unit
202 Input unit
203 Alarm sending unit
210 Telephone line
220 Security company
300 Chest/abdominal motion signal detection device
300a Main body
310 Fixed section
320 Motion section
321 Spring
330 Sensor unit
331 Motion position sensor
331a Detection sensor
331b Signal line
332 Movable piece
340 Signal detection circuit
350 Bluetooth transmitter
360 Power supply unit

The invention claimed is:

1. A digital real security system comprising:
abdominal pressure signal acquiring means for acquiring an abdominal pressure signal from an abdominal pressure sensor for detecting an abdominal pressure of personnel to which the abdominal pressure sensor is fitted;
abdominal pressure signal extracting means for extracting from the acquired abdominal pressure signal an abdominal pressure pattern in which abdominal pressure changes and/or a number of breathing times per unit time;
storage means for storing a normal-time abdominal pressure pattern and/or number of breathing times of the personnel extracted by the abdominal pressure signal extracting means in association with the personnel;
abnormality determining means for matching the abdominal pressure pattern and/or number of breathing times extracted by the abdominal pressure signal extracting means to the personnel's normal-time abdominal pressure pattern and/or number of breathing times stored in the storage means, and determining whether it is abnormality based on the match result; and
control means for reporting an abnormal situation according to the abnormality determination result by the abnormality determining means,
wherein
the abdominal pressure signal acquiring means further acquires a respiration signal from a respiration sensor for detecting breathing of the personnel, and
the abdominal pressure signal extracting means subtracts the respiration signal component from the acquired abdominal pressure signal, and extracts an abdominal pressure pattern from an abdominal pressure signal with suppressed influence of respiration.

2. The digital real security system according to claim 1, wherein the abnormality determining means determines that it is abnormality if the match result of the abdominal pressure pattern and/or number of breathing times extracted by the abdominal pressure signal extracting means with the personnel's normal-time abdominal pressure pattern and/or number of breathing times stored in the storage means is a mismatch.

3. The digital real security system according to claim 1, wherein the control means makes a different report according to the abnormality determination result of the abnormality determining means.

4. The digital real security system according to claim 1, wherein the reporting means transmits an e-mail message and an image.

5. A tangible non-transitory computer-readable storage medium having a program stored therein, wherein the program configures a computer to perform as the digital real security system according to claim 1.

6. A digital real security method comprising:
an abdominal pressure signal acquiring step of acquiring an abdominal pressure signal from an abdominal pressure sensor for detecting an abdominal pressure of personnel to which the abdominal pressure sensor is fitted;
an abdominal pressure signal extracting step of extracting from the acquired abdominal pressure signal an abdominal pressure pattern in which abdominal pressure changes and/or a number of breathing times per unit time;
a storing step of storing a normal-time abdominal pressure pattern and/or number of breathing times of the personnel extracted by the abdominal pressure signal extracting step in association with the personnel;
an abnormality determining step of matching the abdominal pressure pattern and/or number of breathing times extracted by the abdominal pressure signal extracting step to the personnel's normal-time abdominal pressure pattern and/or number of breathing times stored by the storing step, and determining whether it is abnormality based on the match result; and a control step of reporting an abnormal situation according to the abnormality determination result by the abnormality determining step, wherein the abdominal pressure signal acquiring step further acquires a respiration signal from a respiration sensor for detecting breathing of the personnel, and the abdominal pressure signal extracting step subtracts the respiration signal component from the acquired abdominal pressure signal, and extracts an abdominal pressure pattern from an abdominal pressure signal with suppressed influence of respiration.

\* \* \* \* \*